United States Patent [19]

Chen et al.

[11] Patent Number: 6,127,563
[45] Date of Patent: Oct. 3, 2000

[54] INTEGRATED PROCESS FOR PREPARATION OF DIENE COMPLEXES

[75] Inventors: Eugene Y. Chen; David D. Devore; Richard E. Campbell, Jr.; D. Patrick Green; Jasson T. Patton; Jorge Soto; David R. Wilson, all of Midland, Mich.

[73] Assignee: The Dow Chemical Company, Midland, Mich.

[21] Appl. No.: 09/420,626

[22] Filed: Oct. 20, 1999

Related U.S. Application Data

[62] Division of application No. 09/265,641, Mar. 10, 1999
[60] Provisional application No. 60/077,489, Mar. 11, 1998, and provisional application No. 60/091,207, Jun. 30, 1998.

[51] Int. Cl.$^7$ .............................. C07F 17/00; C07F 7/00; C07F 9/02
[52] U.S. Cl. ............................... 556/21; 556/22; 556/23; 556/52; 526/160; 526/943; 502/103; 502/117
[58] Field of Search ................................. 556/21, 23, 22, 556/52; 502/103, 117; 526/160, 943

[56] References Cited

U.S. PATENT DOCUMENTS

| | | | |
|---|---|---|---|
| 5,198,401 | 3/1993 | Turner et al. | 502/155 |
| 5,470,993 | 11/1995 | Devore et al. | 556/11 |
| 5,491,246 | 2/1996 | Rosen et al. | 556/7 |
| 5,512,693 | 4/1996 | Rosen et al. | 556/7 |
| 5,527,929 | 6/1996 | Timmers et al. | 556/7 |
| 5,679,816 | 10/1997 | Timmers et al. | 556/53 |

OTHER PUBLICATIONS

Yasuda et al., Acc. Chem. Res., vol. 18, pp. 120–126, 1985.
Ecker et al., Adv. Organomet. Chem.,vol. 24, pp. 1–39, 1985
Ecker et al., Chem. Ber., vol. 127, pp. 805–811, 1994.
Chemical Abstracts, vol. 127, No. 5, Aug. 4, 1997, Abstract 331, 554.
Chemical Abstracts, vol. 127, No. 5, Aug. 4, 1997, Abstract 65,863.
Malcolm Green et al.,J. Orgamomet. Chem., 462(1–2, 1993.
Gary Diamond et al.,J. Chem. Soc., (17), 2641–2646, 1992.
Chemical Abstracts, vol. 115, No. 21, Nov. 25, 1991, Abstract 232,408.
Yasuda, et al., Organometallics, 1982, 1, 388–396, (Yasuda I).
J. Chem. Soc., Chem. Comm., 1989, 24, 1865–1867.
Inorg. Chem., 1981, 20, 1844–1849.

Primary Examiner—Porfirio Nazario-Gonzalez

[57] ABSTRACT

Disclosed is a process for preparing bridged Group 4 metal complexes containing a neutral diene ligand starting from the corresponding novel, metal diene containing complexes by reaction thereof with the divalent derivative of a bridged bidentate ligand compound. The novel, intermediate metal diene complexes, their formation from tetravalent metal salts and an integrated process combining both process steps are claimed.

4 Claims, No Drawings

6,127,563

INTEGRATED PROCESS FOR PREPARATION OF DIENE COMPLEXES

CROSS-REFERENCE

This is a divisional application of U.S. application Ser. No. 09/265,641, filed Mar. 10, 1999, which claims benefit from provisional applications 60/077,489, filed Mar. 11, 1998 and 60/091,207, filed Jun. 30, 1998.

BACKGROUND OF THE INVENTION

This invention relates to a process for preparing certain Group 4 transition metal complexes possessing neutral diene ligands. The complexes are useful as components or precursors of components in addition polymerization catalysts used in preparing polyolefins, especially crystalline polypropylene.

The preparation and characterization of certain biscyclopentadienyl zirconium and hafnium diene complexes is described in the following references: Yasuda, et al., *Organometallics,* 1982, 1, 388 (Yasuda I); Yasuda, et al. *Acc. Chem. Res.,* 1985, 18 120 (Yasuda II); Erker, et al., *Adv. Organomet. Chem.,* 1985, 24, 1 (Erker I); Erker et al. *Chem. Ber.,* 1994, 127, 805 (Erker II); and U.S. Pat. No. 5,198,401. Certain of the present metal diene complexes and methods for preparing the same have been previously disclosed in U.S. Pat. Nos. 5,512,693, 5,527,929, and 5,679,816. U.S. Pat. Nos. 5,470,993 and 5,491,246 disclosed monocyclopentadienyl diene complexes with titanium or zirconium in which the metal is in the +2 formal oxidation state. Such metal complexes were formed by contacting a metal complex with a source of the cyclopentadienyl dianion ligand, a reducing agent and the neutral diene compound in any order.

In *J. Chem. Soc., Chem. Comm.,* 24, 1865–1867 (1989) zirconium and hafnium dichloride complexes of 2,3-dimethyl-1-3-butadiene were disclosed. The complexes were also converted to the corresponding non-bridged bis (indenyl) derivatives. In *Inorg. Chem,* 1981, 20, 1844–1849, complexes of the type $[ZrCl_3(PR_3)_2]_2$ which were shown to be chloride bridging dimers, were prepared by reducing $ZrCl_4(PR_3)_2$ with sodium amalgam.

SUMMARY OF THE INVENTION

The present invention relates to a process for preparing a metal complex corresponding to the formula:

(L—A—L)MD, or a Lewis base adduct thereof, comprising, contacting in any order a Group 4 metal complex corresponding to the formula $MX_2D$ or a Lewis base adduct thereof, and a compound of the formula: $(L—A—L)M''_n$; wherein:

M is titanium, zirconium or hafnium in the +2 formal oxidation state;

M" is hydrogen or a Group 1 metal cation, a Group 2 metal or zinc dication, a magnesium- or zinc monohalide cation, a tri($C_{1-20}$ hydrocarbyl)silyl group, a mono ($C_{1-20}$ hydrocarbyl)aluminum group; a di($C_{1-20}$ hydrocarbyl)aluminum group; or a mono($C_{1-20}$ hydrocarbyl)zinc group, with the proviso that M" is labile under the reaction conditions;

L is an anionic ligand group bonded to A, except in the formula $(L—A—L)M''_n$ when M" is hydrogen or silyl, L is a neutral ligand group bonded to A, said L group containing up to 50 atoms other than hydrogen;

A is a divalent bridging group joining two L groups;

D is a neutral, substituted derivative of 1,3-butadiene, substituted with one or more hydrocarbyl groups, silyl groups, hydrocarbylsilyl groups, silylhydrocarbyl groups, or mixtures thereof, at least one of said substituents being located at the 1- or 4-position, said D having from 5 up to 40 atoms other than hydrogen;

X independently each occurrence is a monovalent anionic leaving group of up to 50 atoms other than hydrogen, and optionally, two X groups are joined together thereby forming a divalent anionic leaving group; and n is 1 or 2, and recovering the resulting product.

Advantageously, when the L groups are chosen such that the resulting complexes possess more than one isomer, the foregoing process results in the production of primarily the racemic isomer of the metal complex (L—A—L)MD, or its Lewis base adduct. Preferably, products containing greater than 60 mole percent, more preferably greater than 70 mole percent of the racemic isomer are formed without use of purification or isomer separation techniques. The process is capable of producing the racemic isomer in essentially pure form and in high yields. Such racemic isomer products are highly desirable for use as catalyst components in preparing isotactic polyolefins such as polypropylene.

This result is believed to be due to the unique chemical properties of the starting reactant which is a novel composition of matter. Consequently, the invention additionally comprises novel metal complexes corresponding to the formula: $MX_2D$ or a Lewis base adduct thereof, wherein, M is titanium, zirconium or hafnium in the +2 formal oxidation state;

D is a neutral, substituted derivative of 1,3-butadiene, substituted with one or more hydrocarbyl groups, silyl groups, hydrocarbylsilyl groups, silylhydrocarbyl groups, or mixtures thereof, at least one of said substituents being located at the 1- or 4-position, said D having from 5 up to 40 atoms other than hydrogen; and X independently each occurrence is a monovalent anionic leaving group of up to 50 atoms other than hydrogen, and optionally, two X groups are joined together thereby forming a divalent anionic leaving group.

Additionally according to the present invention there is provided a novel process for preparing the foregoing Group 4 metal complex corresponding to the formula $MX_2D$ or a Lewis base adduct thereof, the steps of the process comprising contacting in any order, in an inert diluent, and optionally in the presence of a Lewis base, a Group 4 metal complex corresponding to the formula, $M^1X_4$, or $M^1X_4(L')_k$ with a compound corresponding to the formula $D'M'''_{n'}$; wherein, $M^1$ is titanium, zirconium or hafnium in the +4 formal oxidation state;

X independently each occurrence is a monovalent anionic leaving group of up to 50 atoms other than hydrogen, and optionally, two X groups are joined together thereby forming a divalent anionic leaving group;

L' is a Lewis base;

k is a number from 0 to 3;

D' is a divalent derivative of a substituted 1,3-butadiene which is substituted with one or more hydrocarbyl groups, silyl groups, hydrocarbylsilyl groups, silylhydrocarbyl groups, or mixtures thereof, at least one of said substituents being located at the 1- or 4-position, and said D' having from 5 up to 40 atoms other than hydrogen;

M''' is a Group 1 metal cation, a Group 2 metal or zinc dication, a magnesium- or zinc monohalide cation, a mono($C_{1-20}$ hydrocarbyl)aluminum group; a di($C_{1-20}$ hydrocarbyl)aluminum group; or a mono($C_{1-20}$ hydrocarbyl)zinc group; and n' is 1 or 2.

Further additionally according to the present invention there is provided another novel process for preparing the foregoing Group 4 metal complex corresponding to the formula $MX_2D$ or a Lewis base adduct thereof, the steps of the process comprising contacting in any order, in an inert diluent, and optionally in the presence of a Lewis base, a Group 4 metal complex corresponding to the formula, $M^1X_4$, or $M^1X_4(L')_k$ with a reducing agent to prepare a dimeric compound corresponding to the formula:

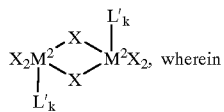, wherein

M is titanium, zirconium or hafnium in the +2 formal oxidation state;

$M^1$ is titanium, zirconium or hafnium in the +4 formal oxidation state;

$M^2$ is titanium, zirconium or hafnium in the +3 formal oxidation state;

X independently each occurrence is a monovalent anionic leaving group of up to 50 atoms other than hydrogen, and optionally, two X groups (excluding bridging anion X groups) are joined together thereby forming a divalent anionic leaving group L' is a Lewis base, and k is a number from 0 to 3.

Compounds of the formula $MX_2D(L')_k$ are thereafter formed by subsequently or simultaneously contacting said dimeric compound with the diene D, wherein D is as previously defined. In the process, the dimeric compound disproportionates thereby forming the diene compound, $MX_2D(L')_k$, and regenerated starting reagent, $M^1X_4(L')_k$. If the initial reduction is conducted in the presence of the diene, D, using excess reducing agent, the process will continue through numerous iterations, producing primarily easily separated salt byproducts and the desired diene product, $MX_2D(L')_k$, resulting in a process that is extremely efficient.

Highly preferably, the reducing agent in the foregoing process is an alkali metal or alkali metal alkyl, most preferably lithium or lithium alkyl, and the inert diluent is a hydrocarbon liquid, most preferably an aliphatic or aromatic hydrocarbon. Using such diluents, excess reducing agent, particularly lithium, will not react with the diene, thereby avoiding a competing and less efficient reaction mechanism to form the desired product.

Finally, according to the present invention there are provided integrated processes incorporating the foregoing individual processes in varying combination. Thus, one process for preparing a metal complex corresponding to the formula,

or a Lewis base adduct thereof, comprises the steps of:

A) forming a Group 4 metal complex corresponding to the formula $MX_2D$ or a Lewis base adduct thereof by contacting in any order, in an inert diluent, and optionally in the presence of a Lewis base, a Group 4 metal complex corresponding to the formula $M^1X_4$, or $M^1X_4(L')_k$ with a complex corresponding to the formula $D'M'''_{n'}$;

B) contacting the resulting complex, $MX_2D$, or the Lewis base adduct thereof, in any order, in an inert diluent, and optionally in the presence of a Lewis base, with a derivative of a bridged ligand corresponding to the formula (L—A—L)$M''_n$; and C) recovering the desired metal complex, wherein:

M is titanium, zirconium or hafnium in the +2 formal oxidation state;

M' is titanium, zirconium or hafnium in the +4 formal oxidation state;

M'' is hydrogen or a Group 1 metal cation, a Group 2 metal or zinc dication, a magnesium or zinc monohalide cation, a tri($C_{1-20}$ hydrocarbyl)silyl group, a mono ($C_{1-20}$ hydrocarbyl)aluminum group; a di($C_{1-20}$ hydrocarbyl)aluminum group; or a mono($C_{1-20}$ hydrocarbyl)zinc group, with the proviso that M'' is labile under the reaction conditions;

M''' is a Group 1 metal cation, a Group 2 metal or zinc dication, a magnesium or zinc monohalide cation, a mono($C_{1-20}$ hydrocarbyl)aluminum group; a di($C_{1-20}$ hydrocarbyl)aluminum group; or a mono($C_{1-20}$ hydrocarbyl)zinc group;

D is a neutral, substituted derivative of 1,3-butadiene, substituted with one or more hydrocarbyl groups, silyl groups, hydrocarbylsilyl groups, silylhydrocarbyl groups, or mixtures thereof, at least one of said substituents being located at the 1- or 4-position, said D having from 5 up to 40 atoms other than hydrogen;

D' is a divalent derivative of D;

X independently each occurrence is a monovalent anionic leaving group of up to 50 atoms other than hydrogen, and optionally, two X groups are joined together thereby forming a divalent anionic leaving group;

L is an anionic ligand group bonded to A, except in the formula (L—A—L)$M''_n$, when M'' is hydrogen or silyl, L is a neutral ligand group bonded to A, said L group containing up to 50 atoms other than hydrogen;

A is a divalent bridging group joining two L groups;

L' is a Lewis base, k is a number from 0 to 3, n is 1 or 2, and n' is 1 or 2.

Another integrated process for preparing a metal complex corresponding to the formula,

or a Lewis base adduct thereof, comprises the steps of:

A) forming a Group 4 metal complex corresponding to the formula $MX_2D$ or a Lewis base adduct thereof by contacting in any order, in an inert diluent, and optionally in the presence of a Lewis base, a Group 4 metal complex corresponding to the formula $M^1X_4$, or $M^1X_4$ (L')$_k$ with a diene, D, in the presence of a reducing agent;

B) contacting the resulting complex, $MX_2D$, or the Lewis base adduct thereof, in any order, in an inert diluent, and optionally in the presence of a Lewis base, with a derivative of a bridged ligand corresponding to the formula (L—A—L)M"$_n$; and C) recovering the desired metal complex, wherein:

M, M$^1$, M", D, X, L, A, L', k, and n are as previously defined.

DETAILED DESCRIPTION

All references to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups. Where citation is made herein to any publication, patent application or provisional patent application, the contents thereof are incorporated herein in their entirety by reference.

Preferred metals, M, M$^1$ and M$^2$ are hafnium and zirconium, most preferably zirconium. Preferred M" groups are Li$^+$, K$^+$, Na$^+$, and Grignard cations. Preferred M'" groups are also Li$^+$, K$^+$, Na$^+$, and Grignard cations.

The L moieties may be the same or different. Examples of suitable L groups include divalent anionic ligands, anionic ligand groups also containing a pair of unshared electrons, which unshared pair of electrons is capable of forming a coordinate/covalent bond to M in the resulting complexes, and unsaturated anionic groups containing delocalized electrons which form a covalent bond to M in the resulting complexes. More specific examples include cyclic ligands containing delocalized electrons, ligands containing allylic functionality and ligand groups containing one or more amino-, phosphino-, amido-, or phosphido-groups. Preferred L groups are cyclic (including polycyclic) hydrocarbyl groups or heteroatom containing hydrocarbyl groups, or such groups further substituted with one or more substituents independently selected from the group consisting of hydrocarbyl, silyl, tri(hydrocarbyl)silyl, tri(hydrocarbyl)germyl, halo, cyano, halohydrocarbyl, halocarbyl, N,N-di(hydrocarbyl)amino, hydrocarbyloxy, and tri(hydrocarbyl)siloxy, said substituent having up to 20 atoms other than hydrogen, or optionally, two such substituents may be bonded together. More specifically, such L groups include cyclopentadienyl, indenyl, fluorenyl, cyclohexadienyl, cycloheptadienyl, benzoindenyl, boratabenzenyl, s-indacenyl, gem-dimethylacenaphthalenyl, and cyclopenta(I)phenanthrenyl groups, as well as substituted derivatives thereof bearing one or more substituents independently selected from the group consisting of hydrocarbyl, silyl, tri(hydrocarbyl)silyl; tri(hydrocarbyl)germyl, halo, cyano, halohydrocarbyl, halocarbyl, N,N-di(hydrocarbyl)amino, hydrocarbyloxy, and tri(hydrocarbyl)siloxy, said substituent having up to 20 atoms other than hydrogen, or optionally, two such substituents may be bonded together.

For further elucidation and explication and not to be limited thereby, the latter mentioned ring systems are illustrated as follows:

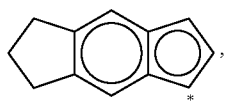

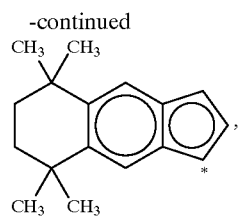

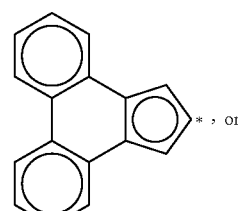

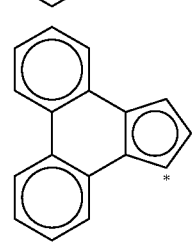

wherein the * indicates the preferred position for attachment of A.

Preferred substituents on L are C$_{1-10}$ hydrocarbyl, C$_{1-10}$ halohydrocarbyl, tri(C$_{1-6}$hydrocarbyl)silyl groups, and N,N-di(C$_{1-4}$ hydrocarbyl)amino groups. Highly preferred L groups are cyclopentadienyl, tetramethylcyclopentadienyl, inden-1-yl, 2-methylinden-1-yl, 2-methyl-4-phenylinden-1-yl, 2-methyl-4-(3,5-bis(trifluoromethyl)phenyl)inden-1-yl, 2,4,6,7-tetramethylinden-1-yl, 2-methyl-4-(1-naphthyl)indene-1-yl, 3,4-cyclopenta(I)phenanthrenyl, 2,3-cyclopenta(1)phenanthrenyl, and 2-methyl-4,5-benzoinden-1-yl.

The A grouping is any divalent ligand group able to bond to two L groups. Preferred bridging groups are those corresponding to the formula (ER'"$_2$)$_x$ wherein E is carbon, silicon or germanium, R'" independently each occurrence is hydrogen or a group selected from silyl, hydrocarbyl, hydrocarbyloxy and combinations thereof, or two R'" groups together form a ring system, said R'" having up to 30 atoms other than hydrogen, and x is an integer from 1 to 8. Preferably R'" independently each occurrence is hydrogen, methyl, methoxy, benzyl, tert-butyl or phenyl. A most highly preferred A group is dimethylsilanediyl or 1,2-ethanediyl.

Examples of suitable D ligands include: η$^4$-1,4-diphenyl-1,3-butadiene; η$^4$-1,3-pentadiene; η$^4$-1-phenyl-1,3-pentadiene; η$^4$-1,4-dibenzyl-1,3-butadiene; η$^4$-2,4-hexadiene; η$^4$-3-methyl-1,3-pentadiene; η$^4$-1,4-ditolyl-1,3-butadiene; and η$^4$-1,4-bis(trimethylsilyl)-1,3-butadiene. Of the foregoing complexes, terminally di-substituted derivatives (that is, the 1,4-disubstituted 1,3-butadienes are preferred. A most preferred D ligand is 1,4-diphenyl-1,3-butadiene.

Preferred Group 4 metal reagents include the well known tetrahalide, tetralkoxide, β-diketonate, and tetrakis(N,N-dialkyl)amide salts, their Lewis base adducts, as well as mixed salts containing mixtures of halide, alkoxide, β-diketonate, and amide ligand groups. In addition to the use of the specified Group 4 metal salt the skilled artisan will appreciate that the same result can be obtained by utilizing instead the corresponding salt in the +3 formal oxidation state, and using an oxidizing agent to increase the oxidation state of the metal at the same time, thereby generating the +4 oxidation state metal complex in situ, or reducing the starting +3 salt directly to the +2 oxidation state. Examples of suitable oxidizing agents include ferrocenium ion, $Pb^{+2}$, $Ag^{+1}$, and halohydrocarbons, such as methyl chloride, methylene chloride, chloroform, carbon tetrachloride or perchloroethylene.

The metal salts used as reactants in the present invention of the formula $MX_2D$, $M^1X_4$ or their corresponding Lewis base adducts are preferably Group 4 metal halide complexes. Highly preferred are compounds containing from 1 to 2, more preferably 2, Lewis base ligands. Preferred Lewis bases are ethers, amines, diamines, triamines, phosphines and thioethers, containing up to 30 atoms other than hydrogen. Especially preferred are trihydrocarbylamines and trihydrocarbylphosphines containing from 1 to 20 carbons in each hydrocarbyl group, most preferably trialkylphosphines, and most highly preferably trimethylphosphine, triethylphosphine, tri-n-propylphosphine, triisopropylphosphine or tri-n-butylphosphine. The Lewis base provides desired stabilization to the metal complex intermediate, e.g., complexes of the formula, $MX_2D$.

In as much as the resulting complexes of the formula (L—A—L)MD are relatively stable even in the absence of a Lewis base, in the event the Lewis base is utilized to stabilize the intermediate complex, $MX_2D$, it is generally highly desirable in order not to affect the catalytic properties of the resulting metal complexes, to subsequently remove the Lewis base from the product, suitably by devolatilization or solubility difference, especially filtration or recrystallization. The Lewis base may be recovered and recycled thereby reducing the cost of such component in the process.

Preferred complexes formed by the present invention correspond to the formula:

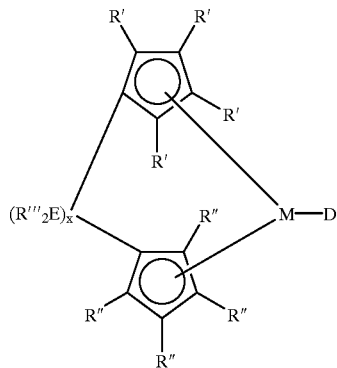

wherein:

M, D, E, R''' and x are as previously defined, and R' and R'' in each occurrence are independently hydrogen, hydrocarbyl, halocarbyl, halohydrocarbyl, silyl, tri(hydrocarbyl)silyl, hydrocarbyloxy, tri(hydrocarbyl)siloxy, N,N-dihydrocarbylamino, N,N-bis(trihydrocarbylsilyl)amino, cyano, or halo, said R' or R'' each having up to 20 atoms other than hydrogen, or adjacent R' groups and/or adjacent R'' groups are joined together thereby forming a divalent derivative.

Such bridged structures are especially suited for use in catalyst compositions in combination with an activator compound for the preparation of polymers having stereoregular molecular structure. In such capacity it is preferred that the metal complex possesses at least pseudo $C_s$ symmetry or possess a chiral, stereorigid structure having at least pseudo $C_2$ symmetry. By "at least pseudo $C_S$ symmetry" is meant that one L group is bulkier (larger) than the other, thereby causing monomer to be selectively incorporated into the polymer chain, such that the resulting polymer has increased stereoregularity. It is also preferred that the R' and R'' substituents are symmetrically distributed about their respective rings as depicted in the foregoing structure with respect to a plane which bisects the ring through the atom thereof bonded to the bridging group, and is perpendicular to the plane of the ring. Examples of complexes possessing at least pseudo $C_s$ symmetry are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). By a chiral structure possessing "at least pseudo $C_2$ symmetry" is meant that the R' or R'' substituents respectively are unsymmetrically distributed about their respective rings in the foregoing figure with respect to a plane which bisects the ring through the atom thereof bonded to the bridging group and is perpendicular to the plane of the ring such that the metal complex has a racemic structure, as opposed to a meso structure. It is preferred that for each cyclic group the R' or R'' substituents on one side of the plane that bisects it are much bulkier (larger) than the R' or R'' substituents on the other side of the plane. Examples of such chiral structures include racemic bis-indenyl complexes. Similar systems based on Ti(IV) or Zr(IV) were disclosed for preparation of isotactic olefin polymers in Wild et al., *J. Organomet. Chem*, 232, 233–47, (1982).

Exemplary metal complexes of the formula, (L—A—L)MD, are: dimethylsilanediyl-bis(inden-1-yl)zirconium($\eta^4$-1,4-diphenyl-1,3-butadiene), dimethylsilanediyl-bis(2-methylinden-1-yl)zirconium($\eta^4$, -1,4-diphenyl-1,3-butadiene), dimethylsilanediyl-bis(2,3-dimethylinden-1-yl) zirconium($\eta^4$-1,4-diphenyl-1,3-butadiene), dimethylsilanediyl-bis(2-methyl-4-phenylinden-1-yl) zirconium($\eta^4$-1,4-diphenyl-1,3-butadiene), dimethylsilanediyl-bis(2-methyl-4-(3,5-bis(trifluoromethyl)phenyl)inden-1-yl)zirconium($\eta^4$-1-4-diphenyl-1,3-butadiene), dimethylsilanediyl-bis(2-methyl-4-(1-naphthyl)inden-1-yl)zirconium($\eta^4$-1,4-diphenyl-1,3-butadiene), dimethylsilanediylbis(2-methyl-4,5-benzoinden-1-yl) zirconium($\eta^4$-1,4-diphenyl-1,3-butadiene), dimethylsilanediylbis(4,5,6,7-tetrahydroinden-1-yl) zirconium($\eta^4$-1,4-diphenyl-1,3-butadiene), dimethylsilanediylbis(2-methylindacen-1-yl)zirconium($\eta^4$-1,4-diphenyl-1,3-butadiene), dimethylsilanediylbis($\eta^8$-2,3-dimethyl-s-indacenyl)zirconium($\eta^4$-1,4-diphenyl-1,3-butadiene), dimethylsilanediylbis($\eta^6$-3-phenyl-s-indacenyl) zirconium($\eta^4$-1,4-diphenyl-1,3-butadiene), dimethylsilanediylbis($\eta^6$-3-phenyl-gem-dimethylacenaphthalenyl)zirconium($\eta^4$-1,4-diphenyl-1,3-butadiene), dimethylsilanediylbis($\eta^6$-cyclopenta(I)phenanthren-2-yl)zirconium($\eta^4$-1,4-diphenyl-1,3-butadiene), 1,2-ethanediylbis(inden-1-yl)zirconium($\eta^4$-1,4-diphenyl-1,3-butadiene), 1,2-ethanediylbis(2-methylinden-1-yl) zirconium($\eta^4$-1,4-diphenyl-1,3-butadiene), 1,2-ethanediylbis(2,3-dimethylinden-1-yl)zirconium($\eta^4$-1,4-diphenyl-1,3-butadiene), 1,2-ethanediylbis(2-methyl-4-phenylinden-1-yl)zirconium($\eta^4$-1,4-diphenyl-1,3-butadiene), 1,2-ethanediyl-bis(2-methyl-4-(3,5-bis(trifluoromethyl)phenyl)inden-1-yl)zirconium($\eta^4$-1-4-diphenyl-1,3-butadiene), 1,2-ethanediylbis(2-methyl-4-(1-naphthyl)inden-1-yl)

zirconium(η⁴-1,4-diphenyl-1,3-butadiene), 1,2-ethanediylbis(2-methyl-4,5-benzoinden-1-yl)zirconium(η⁴-1,4-diphenyl-1,3-butadiene), 1,2-ethanediylbis(4,5,6,7-tetrahydroinden-1-yl)zirconium(η⁴-1,4-diphenyl-1,3-butadiene), 1,2-ethanediylbis(2-methylinden-1-yl)zirconium(η⁴-1,4-diphenyl-1,3-butadiene), 1,2-ethanediylbis(η⁵-2,3-dimethyl-s-indacenyl)zirconium(η⁴-1,4-diphenyl-1,3-butadiene), 1,2-ethanediylbis(η⁵-3-phenyl-s-indacenyl)zirconium(η⁴-1,4-diphenyl-1,3-butadiene), 1,2-ethanediylbis(η⁵-3-phenyl-gem-dimethylacenaphthalenylzirconium(η⁴-1,4-diphenyl-1,3-butadiene), 1,2-ethanediylbis(η⁵-cyclopenta(I)phenanthren-2-yl)zirconium(η⁴-1,4-diphenyl-1,3-butadiene);

dimethylsilanediyl-bis(inden-1-yl)hafnium(η⁴-1,4-diphenyl-1,3-butadiene), dimethylsilanediyl-bis(2-methylinden-1-yl)hafnium(η⁴-1,4-diphenyl-1,3-butadiene), dimethylsilanediyl-bis(2,3-dimethylinden-1-yl)hafnium(η⁴-1,4-diphenyl-1,3-butadiene), dimethylsilanediyl-bis(2-methyl-4-phenylinden-1-yl)hafnium(η⁴-1,4-diphenyl-1,3-butadiene), dimethylsilanediyl-bis(2-methyl-4-(3,5-bis(trifluoromethyl)phenyl)inden-1-yl)hafnium(η⁴-1-4-diphenyl-1,3-butadiene), dimethylsilanediyl-bis(2-methyl-4-(1-naphthyl)inden-1-yl)hafnium(η⁴-1,4-diphenyl-1,3-butadiene), dimethylsilanediylbis(2-methyl-4,5-benzoinden-1-yl)hafnium(η⁴-1,4-diphenyl-1,3-butadiene), dimethylsilanediylbis(4,5,6,7-tetrahydroinden-1-yl)hafnium(η⁴-1,4-diphenyl-1,3-butadiene), dimethylsilanediylbis(2-methylindacen-1-yl)hafnium(η⁴-1,4-diphenyl-1,3-butadiene), dimethylsilanediylbis(η⁵-2,3-dimethyl-s-indacenyl)hafnium(η⁴-1,4-diphenyl-1,3-butadiene), dimethylsilanediylbis(η⁵-3-phenyl-s-indacenyl)hafnium(η⁴-1,4-diphenyl-1,3-butadiene), dimethylsilanediylbis(η⁵-3-phenyl-gem-dimethylacenaphthalenyl)hafnium(η⁴-1,4-diphenyl-1,3-butadiene), dimethylacenaphthalenyl)zirconium(η⁴-1,4-diphenyl-1,3-butadiene), dimethylsilanediylbis(η⁵-cyclopenta(I)phenanthren-2-yl)zirconium(η⁴-1,4-diphenyl-1,3-butadiene), 1,2-ethanediylbis(inden-1-yl)zirconium(η⁴-1,4-diphenyl-1,3-butadiene), 1,2-ethanediylbis(2-methylinden-1-yl)zirconium(η⁴-1,4-diphenyl-1,3-butadiene), 1,2-ethanediylbis(2,3-dimethylinden-1-yl)zirconium(η⁴-1,4-diphenyl-1,3-butadiene), 1,2-ethanediylbis(2-methyl-4-phenylinden-1-yl)zirconium(η⁴-1,4-diphenyl-1,3-butadiene), 1,2-ethanediyl-bis(2-methyl-4-(3,5-bis(trifluoromethyl)phenyl)inden-1-yl)zirconium(η⁴-1-4-diphenyl-1,3-butadiene), 1,2-ethanediylbis(2-methyl-4-(1-naphthyl)inden-1-yl)zirconium(η⁴-1,4-diphenyl-1,3-butadiene), 1,2-ethanediylbis(2-methyl-4,5-benzoinden-1-yl)zirconium(η⁴-1,4-diphenyl-1,3-butadiene), 1,2-ethanediylbis(4,5,6,7-tetrahydroinden-1-yl)zirconium(η⁴-1,4-diphenyl-1,3-butadiene), 1,2-ethanediylbis(2-methylinden-1-yl)zirconium(η⁴-1,4-diphenyl-1,3-butadiene), 1,2-ethanediylbis(η⁵-2,3-dimethyl-s-indacenyl)zirconium(η⁴-1,4-diphenyl-1,3-butadiene), 1,2-ethanediylbis(η⁶-3-phenyl-s-indacenyl)zirconium(η⁴-1,4-diphenyl-1,3-butadiene), 1,2-ethanediylbis(η⁵-3-phenyl-gem-dimethylacenaphthalenylzirconium(η⁴-1,4-diphenyl-1,3-butadiene), 1,2-ethanediylbis(η⁵-cyclopenta(I)phenanthren-2-yl)zirconium(η⁴-1,4-diphenyl-1,3-butadiene);

dimethylsilanediyl-bis(inden-1-yl)hafnium(η⁴-1,4-diphenyl-1,3-butadiene), dimethylsilanediyl-bis(2-methylinden-1-yl)hafnium(η⁴-1,4-diphenyl-1,3-butadiene), dimethylsilanediyl-bis(2,3-dimethylinden-1-yl)hafnium(η⁴-1,4-diphenyl-1,3-butadiene), dimethylsilanediyl-bis(2-methyl-4-phenylinden-1-yl)hafnium(η⁴-1,4-diphenyl-1,3-butadiene), dimethylsilanediyl-bis(2-methyl-4-(3,5-bis(trifluoromethyl)phenyl)inden-1-yl)hafnium(η⁴-1-4-diphenyl-1,3-butadiene), dimethylsilanediyl-bis(2-methyl-4-(1-naphthyl)inden-1-yl)hafnium(η⁴-1,4-diphenyl-1,3-butadiene), dimethylsilanediylbis(2-methyl-4,5-benzoinden-1-yl)hafnium(η⁴-1,4-diphenyl-1,3-butadiene), dimethylsilanediylbis(4,5,6,7-tetrahydroinden-1-yl)hafnium(η⁴-1,4-diphenyl-1,3-butadiene), dimethylsilanediylbis(2-methylindacen-1-yl)hafnium(η⁴-1,4-diphenyl-1,3-butadiene), dimethylsilanediylbis(η⁵-2,3-dimethyl-s-indacenyl)hafnium(η⁴-1,4-diphenyl-1,3-butadiene), dimethylsilanediylbis(η⁵-3-phenyl-s-indacenyl)hafnium(η⁴-1,4-diphenyl-1,3-butadiene), dimethylsilanediylbis(η⁶-3-phenyl-gem-dimethylacenaphthalenyl)hafnium(η⁴-1,4-diphenyl-1,3-butadiene), dimethylsilanediylbis(η⁵-cyclopenta(I)phenanthren-2-yl)hafnium(η⁴-1,4-diphenyl-1,3-butadiene), 1,2-ethanediylbis(inden-1-yl)hafnium(η⁴-1,4-diphenyl-1,3-butadiene), 1,2-ethanediylbis(2-methylinden-1-yl)hafnium(η⁴-1,4-diphenyl-1,3-butadiene), 1,2-ethanediylbis(2,3-dimethylinden-1-yl)hafnium(η⁴-1,4-diphenyl-1,3-butadiene), 1,2-ethanediylbis(2-methyl-4-phenylinden-1-yl)hafnium(η⁴-1,4-diphenyl-1,3-butadiene), 1,2-ethanediyl-bis(2-methyl-4-(3,5-bis(trifluoromethyl)phenyl)inden-1-yl)hafnium(η⁴-1-4-diphenyl-1,3-butadiene)1,2-ethanediylbis(2-methyl-4-(1-naphthyl)inden-1-yl)hafnium(η⁴-1,4-diphenyl-1,3-butadiene), 1,2-ethanediylbis(2-methyl-4,5-benzoinden-1-yl)hafnium(η⁴-1,4-diphenyl-1,3-butadiene), 1,2-ethanediylbis(4,5,6,7-tetrahydroinden-1-yl)hafnium(η⁴-1,4-diphenyl-1,3-butadiene), 1,2-ethanediylbis(2-methylinden-1-yl)hafnium(η⁴-1,4-diphenyl-1,3-butadiene), 1,2-ethanediylbis(η⁵-2,3-dimethyl-s-indacenyl)hafnium(η⁴-1,4-diphenyl-1,3-butadiene), 1,2-ethanediylbis(η⁵-3-phenyl-s-indacenyl)hafnium(η⁴-1,4-diphenyl-1,3-butadiene), 1,2-ethanediylbis(η⁵-3-phenyl-gem-dimethylacenaphthalenylhafnium(η⁴-1,4-diphenyl-1,3-butadiene), 1,2-ethanediylbis(η⁵-cyclopenta(I)phenanthren-2-yl)hafnium(η⁴-1,4-diphenyl-1,3-butadiene);

dimethylsilanediyl-bis(inden-1-yl)titanium(η⁴-1,4-diphenyl-1,3-butadiene), dimethylsilanediyl-bis(2-methylinden-1-yl)titanium(η⁴-1,4-diphenyl-1,3-butadiene), dimethylsilanediyl-bis(2,3-dimethylinden-1-yl)titanium(η⁴-1,4-diphenyl-1,3-butadiene), dimethylsilanediyl-bis(2-methyl-4-phenylinden-1-yl)titanium(η⁴-1,4-diphenyl-1,3-butadiene), dimethylsilanediyl-bis(2-methyl-4-(3,5-bis(trifluoromethyl)phenyl)inden-1-yl)titanium(η⁴-1-4-diphenyl-1,3-butadiene), dimethylsilanediyl-bis(2-methyl-4-(1-naphthyl)inden-1-yl)titanium(η⁴-1,4-diphenyl-1,3-butadiene), dimethylsilanediylbis(2-methyl-4,5-benzoinden-1-yl)titanium(η⁴-1,4-diphenyl-1,3-butadiene), dimethylsilanediylbis(4,5,6,7-tetrahydroinden-1-yl)titanium(η⁴-1,4-diphenyl-1,3-butadiene), dimethylsilanediylbis(2-methylindacen-1-yl)titanium(η⁴-1,4-diphenyl-1,3-butadiene), dimethylsilanediylbis(η⁵-2,3-dimethyl-s-indacenyl)titanium(η⁴-1,4-diphenyl-1,3-butadiene), dimethylsilanediylbis($\eta^5$-3-phenyl-s-indacenyl)titanium($\eta^4$-1,4-diphenyl-1,3-butadiene), dimethylsilanediylbis($\eta^5$-3-phenyl-gem-dimethylacenaphthalenyl)titanium($\eta^4$-1,4-diphenyl-1,3-butadiene), dimethylsilanediylbis($\eta^5$-cyclopenta(I)phenanthren-2-yl)titanium($\eta^4$-1,4-diphenyl-1,3-butadiene), 1,2-ethanediylbis(inden-1-yl)titanium($\eta^4$-1,4-diphenyl-1,3-butadiene), 1,2-ethanediylbis(2-methylinden-1-yl)titanium($\eta^4$-1,4-diphenyl-1,3-butadiene), 1,2-ethanediylbis(2,3-dimethylinden-1-yl)titanium($\eta^4$-1,4-diphenyl-1,3-butadiene), 1,2-ethanediylbis(2-methyl-4-phenylinden-1-yl)titanium($\eta^4$-1,4-diphenyl-1,3-butadiene), 1,2-ethanediyl-bis(2-methyl-4-(3,5-bis(trifluoromethyl)phenyl)inden-1-yl)titanium($\eta^4$-1-4-diphenyl-1,3-butadiene), 1,2-ethanediylbis(2-methyl-4-(1-naphthyl)inden-1-yl)titanium($\eta^4$-1,4-diphenyl-1,3-butadiene), 1,2-ethanediylbis(2-methyl-4,5-benzoinden-1-yl)titanium($\eta^4$-1,4-diphenyl-1,3-butadiene), 1,2-ethanediylbis(4,5,6,7-tetrahydroinden-1-yl)titanium($\eta^4$-1,4-diphenyl-1,3-butadiene), 1,2-ethanediylbis(2-methylinden-1-yl)titanium($\eta^4$-1,4-diphenyl-1,3-butadiene), 1,2-ethanediylbis($\eta^5$-2,3-dimethyl-s-indacenyl)titanium($\eta^4$-1,4-diphenyl-1,3-butadiene), 1,2-ethanediylbis($\eta^5$-3-phenyl-s-indacenyl)titanium($\eta^4$-1,4-diphenyl-1,3-butadiene), 1,2-ethanediylbis($\eta^5$-3-phenyl-gem-dimethylacenaphthalenyltitanium($\eta^4$-1,4-diphenyl-1,3-butadiene), and 1,2-ethanediylbis($\eta^5$-cyclopenta(I)phenanthren-2-yl)titanium($\eta^4$-1,4-diphenyl-1,3-butadiene).

Preferred intermediate complexes formed by the present invention correspond to the formula: $MX_2D(L')_2D$ wherein M is hafnium or zirconium, X is halide, D is 1,4-diphenyl-1,3-butadiene, and L' is trimethylphosphine, triethylphosphine, tri-n-propylphosphine, triisopropylphosphine or tri-n-butylphosphine. More preferred intermediate metal complexes are those wherein X is chloride or bromide. Most preferred intermediate complexes are zirconiumdichloride($\eta^4$-1,4-diphenyl-1,3-butadiene)bis(triethylphosphine), and zirconiumdichloride($\eta^4$-1,4-diphenyl-1,3-butadiene)bis(tri-n-propylphosphine).

In general, the process involves combining the respective reactants, preferably in a solution, optionally while agitating and/or heating above ambient temperature (25° C.). Recovery and purification of the intermediate products when a multiple step reaction is employed may be desirable, but is not required. The process preferably is conducted in an inert, noninterfering solvent at a temperature from −100° C. to 300° C., preferably from −78 to 130° C., most preferably from −40 to 120° C.

Suitable inert, noninterfering solvents for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and the like, $C_{1-4}$ dialkyl ethers, $C_{1-4}$ dialkyl ether derivatives of (poly)alkylene glycols, and tetrahydrofuran. Mixtures of solvents from the foregoing list are also suitable.

The recovery procedure involves separation of the resulting byproducts and devolatilization of the reaction medium. Extraction into a secondary solvent may be employed if desired. Alternatively, if the desired product is an insoluble precipitate, filtration or other separation technique may be employed.

The complexes of the formula (L—A—L)MD, or a Lewis base adduct thereof, are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 20 carbons in each hydrocarbyl or halogenated hydrocarbyl group, more especially perfluornated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium-, sulfonium-, or ferrocenium-salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: U.S. Pat. Nos. 5,132,380, 5,153,157, 5,064,802, 5,321,106, 5,721,185, 5,350,723, and WO97/04234, equivalent to U.S. Ser. No. 08/818,530, filed Mar. 14, 1997.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. A benefit according to the present invention is the discovery that the most efficient catalyst activation using such a combination of tris(pentafluorophenyl)borane/alumoxane mixture occurs at reduced levels of alumoxane. Preferred molar ratios of Group 4 metal complex:tris(pentafluorophenylborane:alumoxane are from 1:1:1 to 1:5:5, more preferably from 1:1:1.5 to 1:5:3. The surprising efficient use of lower levels of alumoxane with the present invention allows for the production of olefin polymers with high catalytic efficiencies using less of the expensive alumoxane cocatalyst. Additionally, polymers with lower levels of aluminum residue, and hence greater clarity, are obtained.

Suitable ion forming compounds useful as cocatalysts in one embodiment of the present invention comprise a cation which is a Bronsted acid capable of donating a proton, and a compatible, noncoordinating anion. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a Lewis bases such as olefin monomer. A noncoordinating anion specifically refers to an anion which when functioning as a charge balancing anion in a cationic metal complex does not transfer an anionic substituent or fragment thereof to said cation thereby forming neutral complexes.

"Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

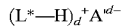

wherein:
L* is a neutral Lewis base;
(L*—H)⁺ is a Bronsted acid;
$A^{d-}$ is a noncoordinating, compatible anion having a charge of d−, and
d is an integer from 1 to 3.

More preferably $A^{d-}$ corresponds to the formula: $[M^*Q_4]^-$;
wherein:
M* is boron or aluminum in the +3 formal oxidation state; and
Q independently each occurrence is selected from hydride, dialkylamido, halide, hydrocarbyl, halohydrocarbyl, halocarbyl, hydrocarbyloxide, hydrocarbyloxy substituted-hydrocarbyl, organometal substituted-hydrocarbyl, organometalloid substituted-hydrocarbyl, halohydrocarbyloxy, halocarbyloxy substituted hydrocarbyl, halocarbyl-substituted hydrocarbyl, and halo-substituted silylhydrocarbyl radicals (including perhalogenated hydrocarbyl- perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this invention may be represented by the following general formula:

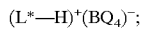

wherein:
L* is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are
tri-substituted ammonium salts such as:
trimethylammonium tetraphenylborate,
methyldioctadecylammonium tetraphenylborate,
triethylammonium tetraphenylborate,
tripropylammonium tetraphenylborate,
tri(n-butyl)ammonium tetraphenylborate,
methyltetradecyloctadecylammonium tetraphenylborate,
N,N-dimethylanilinium tetraphenylborate,
N,N-diethylanilinium tetraphenylborate,
N,N-dimethyl(2,4,6-trimethylanilinium)tetraphenylborate,
trimethylammonium tetrakis(pentafluorophenyl)borate,
methylditetradecylammonium tetrakis(pentafluorophenyl)borate,
methyldioctadecylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,6-trimethylanilinium)tetrakis(pentafluorophenyl)borate,
trimethylammonium tetrakis(2,3,4,6-tetrafluorophenyl)borate,
triethylammonium tetrakis(2,3,4,6-tetrafluorophenyl)borate,
tripropylammonium tetrakis(2,3,4,6-tetrafluorophenyl)borate,
tri(n-butyl)ammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl)borate, and
N,N-dimethyl-(2,4,6-trimethylanilinium)tetrakis-(2,3,4,6-tetrafluorophenyl)borate;
dialkyl ammonium salts such as:
dioctadecylammonium tetrakis(pentafluorophenyl)borate,
ditetradecylammonium tetrakis(pentafluorophenyl)borate, and
dicyclohexylammonium tetrakis(pentafluorophenyl)borate;
tri-substituted phosphonium salts such as:
triphenyiphosphonium tetrakis(pentafluorophenyl)borate,
methyldioctadecylphosphonium tetrakis(pentafluorophenyl)borate, and
tri(2,6-dimethylphenyl)phosphonium tetrakis(pentafluorophenyl)borate.

Preferred are tetrakis(pentafluorophenyl)borate salts of long chain alkyl mono- and disubstituted ammonium complexes, especially $C_{14}$–$C_{20}$ alkyl ammonium complexes, especially methyidi(octadecyl)ammonium tetrakis(pentafluorophenyl)borate and methyidi(tetradecyl)-ammonium tetrakis(pentafluorophenyl)borate, or mixtures including the same. Such mixtures include protonated ammonium cations derived from amines comprising two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

Another suitable ammonium salt, especially for use in heterogeneous catalyst systems is formed upon reaction of a organometal compound, especially a tri($C_{1-5}$-alkyl) aluminum compound with an ammonium salt of a hydroxyaryltris(fluoroaryl)borate compound. The resulting compound is an organometaloxyaryltris(fluoroaryl)borate compound which is generally insoluble in aliphatic liquids. Typically, such compounds are advantageously precipitated on support materials, such as silica, alumina or trialkylaluminum passivated silica, to form a supported cocatalyst mixture. Examples of suitable compounds include the reaction product of a tri($C_{1-6}$ alkyl)aluminum compound with the ammonium salt of hydroxyaryltris(aryl)borate. Suitable hydroxyaryltris(aryl)-borates include the ammonium salts, especially the foregoing long chain alkyl ammonium salts of:

(4-dimethylaluminumoxy-1-phenyl)tris(pentafluorophenyl) borate,
(4-dimethylaluminumoxy-3,5-di(trimethylsilyl)-1-phenyl) tris(pentafluorophenyl)borate,
(4-dimethylaluminumoxy-3,5-di(t-butyl)-1-phenyl)tris (pentafluorophenyl)borate,
(4-dimethylaluminumoxy-1-benzyl)tris(pentafluorophenyl) borate,
(4-dimethylaluminumoxy-3-methyl-1-phenyl)tris (pentafluorophenyl)borate,
(4-dimethylaluminumoxy-tetrafluoro-1-phenyl)tris (pentafluorophenyl)borate,
(5-dimethylaluminumoxy-2-naphthyl)tris (pentafluorophenyl)borate,
4-(4-dimethylaluminumoxy-1-phenyl)phenyltris (pentafluorophenyl)borate,
4-(2-(4-(dimethylaluminumoxyphenyl)propane-2-yl) phenyloxy)tris(pentafluorophenyl)borate,
(4-diethylaluminumoxy-1-phenyl)tris(pentafluorophenyl) borate,
(4-diethylaluminumoxy-3,5-di(trimethylsilyl)-1-phenyl)tris (pentafluorophenyl)borate,
(4-diethylaluminumoxy-3,5-di(t-butyl)-1-phenyl)tris (pentafluorophenyl)borate,
(4-diethylaluminumoxy-1-benzyl)tris(pentafluorophenyl) borate,
(4-diethylaluminumoxy-3-methyl-1-phenyl)tris (pentafluorophenyl)borate,
(4-diethylaluminumoxy-tetrafluoro-1-phenyl)tris (pentafluorophenyl)borate,
(5-diethylaluminumoxy-2-naphthyl)tris(pentafluorophenyl) borate,
4-(4-diethylaluminumoxy-1-phenyl)phenyltris (pentafluorophenyl)borate,
4-(2-(4-(diethylaluminumoxyphenyl)propane-2-yl) phenyloxy)tris(pentafluorophenyl)borate,
(4-diisopropylaluminumoxy-1-phenyl)tris (pentafluorophenyl)borate,
(4-diisopropylaluminumoxy-3,5-di(trimethylsilyl)-1-phenyl)tris(pentafluorophenyl)borate,
(4-diisopropylaluminumoxy-3,5-di(t-butyl)-1-phenyl)tris (pentafluorophenyl)borate,
(4-diisopropylaluminumoxy-1-benzyl)tris (pentafluorophenyl)borate,
(4-diisopropylaluminumoxy-3-methyl-1-phenyl)tris (pentafluorophenyl)borate,
(4-diisopropylaluminumoxy-tetrafluoro-1-phenyl)tris (pentafluorophenyl)borate,
(5-diisopropylaluminumoxy-2-naphthyl)tris (pentafluorophenyl)borate,
4-(4-diisopropylaluminumoxy-1-phenyl)phenyltris (pentafluorophenyl)borate, and
4-(2-(4-(diisopropylaluminumoxyphenyl)propane-2-yl) phenyloxy)tris(pentafluorophenyl)borate.

An especially preferred ammonium compound is methylditetradecylammonium (4-diethylaluminumoxy-1-phenyl) tris(pentafluorophenyl)borate, methyldihexadecylammonium (4-diethylaluminumoxy-1-phenyl)tris (pentafluorophenyl)borate, methyidioctadecyl-ammonium (4-diethylaluminumoxy-1-phenyl)tris(pentafluorophenyl) borate, and mixtures thereof. The foregoing complexes are disclosed in U.S. Pat. Nos. 5,834,393 and 5,783,512.

Another suitable ion forming, activating cocatalyst comprises a salt of a cationic oxidizing agent and a noncoordinating, compatible anion represented by the formula:

$$(Ox^{e+})_d(A^{40\ d-})_e,$$

wherein $Ox^{e+}$ is a cationic oxidizing agent having a charge of e+;
e is an integer from 1 to 3; and
$A'^{d-}$ and d are as previously defined.

Examples of cationic oxidizing agents include: ferrocenium, hydrocarbyl-substituted ferrocenium, $Pb^{+2}$ or $Ag^+$. Preferred embodiments of $A'^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

wherein:

$^+$ is a $C_{1-20}$ carbenium ion; and
$A'^-$ is a noncoordinating, compatible anion having a charge of −1. A preferred carbenium ion is the trityl cation, especially triphenylmethylium.

A further suitable ion forming, activating cocatalyst comprises a compound which is a salt of a silylium ion and a noncoordinating, compatible anion represented by the formula:

$$R_8Si^{+A'-}$$

wherein:

R is $C_{1-10}$ hydrocarbyl; and
$A'^-$ is as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem. Comm.*, 1993, 383–384, as well as Lambert, J. B., et al., *Organometallics*, 1994, 13, 2430–2443. The use of the above silylium salts as activating cocatalysts for addition polymerization catalysts is claimed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are liquids under the conditions of the electrolysis (generally temperatures from 0 to 100° C.), and are capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, $A'^-$; Preferred supporting electrolytes are salts corresponding to the formula $G^+A'^-$; wherein:

$G^+$ is a cation which is nonreactive towards the starting and resulting complex, and $A'^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium-cations.

During activation of the complexes of the present invention by bulk electrolysis the cation of the supporting electrolyte passes to the counter electrode and $A'^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl)borates having from 1 to 10 carbons in each hydrocarbyl or perfluoroaryl group, especially tetra(n-butylammonium)tetrakis(pentafluorophenyl)borate.

The foregoing electrochemical activating technique and activating cocatalysts may also be used in combination. An especially preferred combination is a mixture of a tri (hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 10:1, more preferably from 1:5000 to 10:1, most preferably from 1:1000 to 1:1. Alumoxane, when used by itself as an activating cocatalyst, is preferably employed in large molar ratio, generally at least 100 times the quantity of metal complex on a molar basis. Tris(pentafluorophenyl)borane, where used as an activating cocatalyst is preferably employed in a molar ratio to the metal complex of form 0.5:1 to 10:1, more preferably from 1:1 to 6:1 most preferably from 1:1 to 5:1. The remaining activating cocatalysts are generally preferably employed in approximately equimolar quantity with the metal complex.

The catalysts may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, tetrafluoroethylene, vinylbenzocyclobutane, ethylidenenorbonene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer. Most preferably the present metal complexes are used in the polymerization of propylene to prepare polypropylene having a high degree of isotacticity.

In general, the polymerization may be accomplished at conditions well known in the prior art for Ziegler-Natta or Kaminsky-Sinn type polymerization reactions, such as temperatures from 0–250° C. and pressures from atmospheric to 1000 atmospheres (0.1 to 100 MPa). Suspension, solution, slurry, gas phase or other process conditions may be employed if desired. The support, if present, is preferably employed in an amount to provide a weight ratio of catalyst (based on metal):support from 1:100,000 to 1:10, more preferably from 1:50,000 to 1:20, and most preferably from 1:10,000 to 1:30. Suitable gas phase reactions may utilize condensation of the monomer or monomers employed in the reaction, or of an inert diluent to remove heat from the reactor.

In most polymerization reactions the molar ratio of catalyst:polymerizable compounds employed is from $10^{-12}:1$ to $10^{-1}:1$, more preferably from $10^{-12}:1$ to $10^{-5}:1$.

Suitable solvents or diluents for polymerization via a solution or slurry process are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, 1-butene, 1-pentene, butadiene, cyclopentene, 1-hexene, 3-methyl-1-pentene, 4-methyl-1-pentene, 1,4-hexadiene, 1,7-octadiene, 1-octene, 1-decene, styrene, divinylbenzene, ethylidenenorbonene, allylbenzene, vinyltoluene (including all isomers alone or in admixture), 4-vinylcyclohexene, and vinylcyclohexane. Mixtures of the foregoing are also suitable.

The catalysts may also be utilized in combination with at least one additional homogeneous or heterogeneous polymerization catalyst in the same or in separate reactors connected in series or in parallel to prepare polymer blends having desirable properties. An example of such a process is disclosed in WO 94/00500, equivalent to U.S. Ser. No. 07/904,770, as well as U.S. Pat. No. 5,844,045.

The present catalyst compositions are advantageously employed in a process for preparing homopolymers of propylene, random or block copolymers of propylene and an olefin selected from the group consisting of ethylene, $C_{4-10}$ olefins, and $C_{4-10}$ dienes, and random terpolymers of propylene and olefins selected from the group consisting of ethylene and $C_{4-10}$ olefins. The $C_{4-10}$ olefins include the linear and branched olefins such as, for example, 1-butene, isobutylene, 1-pentene, 3-methyl-1-butene, 1-hexene, 3,4-dimethyl-1-butene, 1-heptene, 1-octene, and 3-methyl-1-hexene. Examples of $C_{4-10}$ dienes include 1,3-butadiene, 1,4-pentadiene, isoprene, 1,5-hexadiene, and 2,3-dimethyl-1,3-hexadiene.

Preferred polypropylene products have a molecular weight (Mw) of at least about 100,000, and a molecular weight distribution, Mw/Mn of less than 3.0, preferably less than 2.5.

The polymerization is generally conducted under continuous or semicontinuous slurry polymerization conditions in hydrocarbons such as propylene, propane, butene, butane, pentane, butene-2, isobutane, hexane, heptane, and mixtures of the foregoing, generally at temperatures from 50 to 100° C., and pressures from atmospheric to 1 MPa. The polymerization may be conducted in one or more continuous stirred tank tubular reactors or fluidized bed, gas phase reactors, connected in series or parallel. Condensed monomer or solvent may be added to the gas phase reactor as is well known in the art. The catalyst may also be supported and/or prepolymerized prior to use.

In a continuous reaction system, the reaction mixture is typically maintained at conditions at which the polymer is produced as a slurry of powder in the reaction mixture. Use of highly active and highly stereospecific catalyst systems in propylene polymerization substantially eliminates the need to remove catalyst components or atactic polymer from the polymer product. The mixture of reaction components is fed continuously or at frequent intervals into the reactor system and is continuously monitored so as to ensure an efficient reaction and the desired product. For example, it is well known that supported coordination catalysts and catalyst systems of the type described above are highly sensitive, in varying degrees, to catalyst poisons such as water, oxygen, carbon oxides, acetylenic compounds and sulfur compounds. Introduction of such compounds may result in reactor upset and production of off-grade product. Typically, computer control systems are used to maintain process variables within acceptable limits, often by measuring polymer variables such as viscosity, density and tacticity, or catalyst productivity.

In the process, reactants and diluents, which may be a mixture of propylene, hydrogen, nitrogen, unreacted comonomers and inert hydrocarbons, are continuously recycled through the reactor, optionally with scavenging to remove impurities and condensation to remove the heat of polymerization. Catalyst and cocatalysts, fresh monomer or comonomer(s) and selectivity control agents, branching agents or chain transfer agents, if desired, are likewise continuously fed to the reactor. The polymer product is continuously or semi-continuously removed and volatile components removed and recycled. Suitable processes for preparing polypropylene polymers are known in the art and illustrated by those taught in U.S. Pat. Nos. 4,767,735, 4,975,403, and 5,084,513, among others.

Utilizing the catalysts of the present invention, copolymers having high comonomer incorporation and correspondingly low density, yet having a low melt index, may be readily prepared. That is, high molecular weight polymers are readily attained by use of the present catalysts, even at elevated reactor temperatures. This result is highly desirable because the molecular weight of α-olefin copolymers can be readily reduced by the use of hydrogen or similar chain transfer agent, however increasing the molecular weight of α-olefin copolymers is usually only attainable by reducing the polymerization temperature of the reactor. Disadvantageously, operation of a polymerization reactor at reduced temperatures significantly increases the cost of operation since heat must be removed from the reactor to maintain the reduced reaction temperature, while at the same time heat must be added to the reactor effluent to vaporize the solvent. In addition, productivity is increased due to improved polymer solubility, decreased solution viscosity, and a higher polymer concentration. Utilizing the present catalysts, α-olefin homopolymers and copolymers having densities from 0.85 g/cm$^3$ to 0.96 g/cm$^3$, and melt flow rates from 0.001 to 1000 dg/min are readily attained in a high temperature process.

The catalyst system may be prepared as a homogeneous catalyst by addition of the requisite components to a solvent in which polymerization will be carried out by solution polymerization procedures. The catalyst system may also be prepared and employed as a heterogeneous catalyst by adsorbing the requisite components on a catalyst support material such as silica, alumina, aluminosilicates, or other suitable inorganic support material, or a polymer, such as preformed olefin polymer. A preferred support material is silica that has been heated (calcined) to 200 to 800° C. for a time sufficient to remove substantially all surface water and thereafter reacted with a Lewis acid, especially a $C_{1-6}$ trialkylaluminum compound to react substantially all available hydroxyl groups. The heterogeneous form of the catalyst system is employed in a slurry polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably the diluent comprises in at least major part the α-olefin monomer or monomers to be polymerized.

The polymerization may be carried out as a batchwise or a continuous polymerization process. A continuous process is preferred, in which event catalyst, α-olefin, and optionally solvent and diene are continuously supplied to the reaction zone and polymer product continuously removed therefrom.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis.

Tetrahydrofuran (THF), diethylether, toluene, and hexane were used following passage through double columns charged with activated alumina and alumina supported mixed metal oxide catalyst (Q-5® catalyst, available from Engelhard Corp.) Grignard reagents and n-BuLi, if recited, were all used as purchased from the supplier. All syntheses were performed under dry nitrogen or argon atmosphere using a combination of glove box and high vacuum techniques. The term "overnight", if used, refers to a time of approximately 16–18 hours. The term "room temperature", if used, refers to a temperature of about 20–25° C. Generally the following examples resulted in the production of metal complexes wherein the molar ratio of rac/meso isomers was greater than 85 percent.

Example 1

Preparation of rac dimethylsilanebis(2-methyl-4-phenylinden-1-yl)zirconium (II) (1,4-diphenyl-1,3-butadiene)

A) Dichloro(1,4-diphenyl-1,3-butadiene)bis(trimethylphosphine)zirconium

In a flask in a glove box, sodium (0.249 g, 10.8 mmol), a catalytic amount of naphthalene (0.066 g, 0.51 mmol), trans,trans-1,4-diphenyl-1,3-butadiene (1.062 g, 5.15 mmol), and 100 mL of dry THF were mixed and stirred about 18 h at 20–25° C. The solvent of the resulting dark purple solution was removed under reduced pressure and the residue was washed twice with dry hexane, then dried under reduced pressure to give 1,4-diphenylbutenediyl disodium.

$^1$H NMR (THF-d$_6$, 23° C.): δ (ppm) 6.35 (t, $^3J_{H-H}$=6.9 Hz, 2H, m-Ph), 6.15 (t, $^3J_{H-H}$=6.9 Hz, 2H, m-Ph), 5.93 (d, $^3J_{H-H}$=7.2 Hz, 4H, o-Ph), 5.17 (t, $^3J_{H-H}$=6.9 Hz, 2H, p-Ph), 4.94 (dd, J$_{a-b}$=10.5 Hz, J$_{b-b'}$=8.7 Hz, 2H, 2H, β-H), 3,77 (dd, J$_{a-b}$=10.5 Hz, 2H, α-H). $^{13}$C NMR (THF-d$_6$, 23° C.): δ (ppm) 145.97 (ipso-C), 129.51 (m-C), 127.94 (m-C), 118.24 (o-C), 109.62 (o-C), 102.88 (p-C), 97.97 (β-C), α-C overlapped with the THF NMR solvent.

To a mixture of the above dark solid in toluene (100 mL) was added a suspension of zirconium tetrachloride (1.20 g, 5.15 mmol) and 2 equivalents of trimethylphosphine (10.3 mL, 1.0 M in toluene, 10.3 mmol) in 10 mL of toluene. The mixture was then stirred for 48 h at 20–25° C. The resulting dark suspension was filtered to afford a purple-green solution and the solvent of the filtrate was removed under reduced pressure to give 1.50 g (56 percent) of the crude product. The product was further purified by adding 100 mL of hexane to the solid and filtering after stirring for ½ h. The insoluble fraction (a green solid) was discarded and the solvent of the filtrate was removed under reduced pressure to give 1.07 g of dichloro(1,4-diphenyl-1,3-butadiene)bis(trimethylphosphine)zirconium as a light purple solid. Yield was 40 percent.

$^1$H NMR (C$_6$D$_6$, 23° C.): δ (ppm) 7.32–7.14 (m, 10H, Ph), 5.90 (d, $^3J_{H-H}$=9.3 Hz. 2H, β-H), 2.95 (d, $^3J_{H-H}$=9.3 Hz, 2H, α-H), 0.90 (s, br, 18H, PMe$_3$). $^{31}$P NMR (C$_6$D$_6$, 23° C.): δ (ppm) −20.22. $^{13}$C NMR (C$_6$D$_6$, 23° C.): δ (ppm) 144.14, 133.18, 129.13, 127.67, 125.35, 123.47, 109.53, 87.64, 13.03.

B) rac-dimethylsilanebis(2-methyl-4-phenylinden-1-yl)(1,4-diphenyl-1,3-butadiene)zirconium In a flask in a glove box, n-butyllithium (14.0 mL, 1.6 M in hexanes, 22.4 mmol) was added dropwise to a solution of dimethylbis(2-methyl-4-phenylinden-1-yl)silane (5.00 g, 10.6 mmol) in 200 mL of a 1:1 mixture of toluene/hexane at 20–25° C. The mixture was then stirred for an additional 12 h at the same temperature and the suspension was filtered. The pale yellow solid was washed twice with hexane, then was dried under reduced pressure to give 4.80 g of dimethylsilanebis(2-methyl-4-phenylindenyl)dilithium as a light yellow powder. Yield was 94 percent.

To the above prepared dilithio salt (0.185 g, 0.38 mmol) was added dichloro(1,4-diphenyl-1,3-butadiene)bis(trimethylphosphine)zirconium (0.200 g, 0.38 mmol), followed by 50 mL of dry toluene. The color of the suspension slowly turned to red after stirring for ½ h and the mixture was allowed to stir for 12 h at 20–25° C. The resulting mixture was filtered to afford a dark red solution, and the solvent of the filtrate was removed under reduced pressure. The residue was rinsed with 5 mL of cold hexane and dried under reduced pressure for a few hours to give 0.282 g of rac-dimethylsilanebis(2-methyl-4-phenylindenyl)(1,4-diphenyl-1,3-butadiene)zirconium, a red brown solid, as the only isomeric product. Yield was 96 percent.

$^1$H NMR (C$_6$D$_6$, 23° C.): δ (ppm) 7.80 (d, $^3J_{H-H}$=8.4 Hz, 2H), 7.29–6.98 (m, 18H), 6.88 (d, $^8J_{H-H}$=6.9 Hz, 2H), 6.76 (d, $^3J_{H-H}$=7.2 Hz, 4H), 5.58 (s, 2H, β-H, Ind), 3.43 (dd, J$_{a-b}$=14.4 Hz, 2H, β-H, diene), 1.68 (s, 6H, α-Me, Ind), 1.63 (dd, 2H, α-H, diene, partially overlapping with α-Me of Ind peak), 1.22 (s, br, hexane residue), 0.88 (s, 6H, Me$_2$Si), 0.88 (s, br, hexane residue). $^{13}$C NMR (C$_6$D$_6$, 23° C.): δ (ppm) 143.81 140.26, 136.33, 128.80, 126.77, 124.75, 124.61, 123.81, 122.77, 120.82, 107.92, 89.56, 85.37, 81.29, 31.91 and 23.00 (hexane residue), 16.71, 14.32, 2.18.

Example 2

Preparation rac dimethylsilanebis(2-methyl-4-phenylinden-1-yl)zirconium (II) (1,4-diphenyl-1,3-butadiene)

In a flask in a glove box, sodium (0.140 g, 6.11 mmol), a catalytic amount of naphthalene (0.079 g, 0.61 mmol), trans,trans-1,4-diphenyl-1,3-butadiene (0.600 g, 2.91 mmol), and 50 mL of dry THF were mixed and stirred about 18 h at 20–25° C. The solvent of the resulting dark purple solution was removed under reduced pressure and the residue was washed twice with dry hexane, then dried under reduced pressure to give 1,4-diphenylbutenediyl disodium.

Toluene (150 mL) was added to the flask and to this was added a suspension of zirconium tetrachloride (0.678 g, 2.91 mmol) and 2 equivalents of trimethylphosphine (5.82 mL, 1.0 M in toluene, 5.82 mmol) in 50 mL of toluene. The mixture was then stirred for 24 h at 20–25° C. The resulting dark suspension was filtered to afford a purple-green solution.

To the above toluene solution, 0.84 g (1.75 mmol) of dimethylsilanebis(2-methyl-4-phenylindenyl)dilithium (from Example 1) was added as a solid. The color of the suspension slowly turned to red after stirring for ½ h and the mixture was allowed to stir for 18 h at 20–25° C. The resulting mixture was filtered to afford a dark red solution, and the solvent of the filtrate was removed under reduced pressure. The residue was taken up into hexane, filtered and isolated by drying under reduced pressure for a few hours. The resulting red-brown solid was rinsed with 5 mL of cold hexane and dried under reduced pressure for a few hours to give 1.05 g of rac-dimethylsilanebis(2-methyl-4-phenylindenyl)(1,4-diphenyl-1,3-butadiene)zirconium, a red brown solid, as the only isomeric product. Yield was 47 percent.

Example 3

Preparation of zirconium (II) dichloride(1,4-diphenyl-1,3-butadiene)bis(trimethylphosphine)

In a flask in a glove box, naphthalene (1.4 g, 10.9 mmol) was dissolved in 15 mL of THF. To the stirred solution, lithium powder (70 mg, 10 mmol) was added. The mixture was stirred for 2 hours. Another 50 mL flask was charged with anhydrous $MgCl_2$ (456 mg, 4.8 mmol) and 10 mL of THF. To this stirred mixture was added the dark green lithium naphthalenide solution from the first flask via syringe. The new mixture was stirred for 4 hours. The stirring was stopped and the magnesium slurry was allowed to settle overnight. The brownish-yellow supernatant was removed via syringe and discarded. To the Mg solid were added 20 mL of fresh THF, followed by a solution prepared with 825 mg (4.0 mmol) of 1,4-phenyl-1,3-butadiene in 10 mL of THF. The new mixture turned purple immediately. In about 5 minutes the mixture was a deep red wine color. The mixture was stirred for 3 hours and the solvent was removed under reduced pressure. The product, Mg diphenylbutene-diyl (estimated to be 4 mmol), was redissolved in 20 mL of toluene and added via syringe to a mixture of $ZrCl_4$ (932 mg, 4 mmol) and $PMe_3$ (8 mL=8 mmol; 1.0 M in toluene) in 22 mL of toluene. This mixture was stirred approximately 3 days at room temperature and the solvent was removed under reduced pressure. The resulting solid was extracted with 5×25 mL hexane, filtered and recovered by removing hexane under reduced pressure, giving 1.27 g (63 percent yield) of the desired product as a grayish purple solid.

Example 4

Preparation of rac dimethylsilanebis(2-methyl-4-phenylinden-1-yl) zirconium (II) (1,4-diphenyl-1,3-butadiene) with recycle of trimethylphosphine Dimethylsilanebis(2-methyl-4-phenylindenyl)dilithium (0.923 g, 1.92 mmol) was combined with dichloro(1,4-diphenyl-1,3-butadiene)bis(trimethylphosphine)zirconium (1.000 g, 1.92 mmol) in an 'O'-ring flask (flask 1). Immediately following the addition of 100 mL of dry toluene the flask was sealed by means of a Teflon stopcock. The resulting brown slurry was allowed to stir at room temperature overnight during which time the color of the reaction mixture changed to red-brown. The flask was removed from the glove box and attached to a high vacuum line. The reaction mixture was frozen by raising a liquid nitrogen bath around the reaction flask. Evacuation removed the gaseous volatiles. After thawing, the liquid components remaining in the reaction flask were transferred under high vacuum to another 'O'-ring flask (flask 2). The devolatilization was continued for about three hours after no more liquid appeared to be present in the reaction flask by visual observation. Both flasks were subsequently removed to the glove box. To flask 1 containing the non-volatile residue were added 50 mL of toluene. The mixture was filtered and the solvent of the filtrate was removed under reduced pressure. The solid residue was washed twice with hexane, then dried under reduced pressure to give 0.76 g of red-brown rac-dimethylsilanebis(2-methyl-4-phenylindenyl)(1,4-diphenyl-1,3-butadiene)zirconium, 52 percent yield.

Example 5

Preparation of zirconium (II) dichloride (1,4-diphenyl-1,3-butadiene)bis(trimethylphosphine)

To flask 2 from Example 4 containing the volatile components was added zirconium tetrachloride (0.4477 g, 1.92 mmol) and the resulting slurry was stirred for about 2 h, then 1,4-diphenylbutenediyl disodium (0.6532 g, 1.92 mmol, effective molecular weight of 340 g/mol determined by titration) was added. No additional source of trimethylphosphine other than the volatile components in flask 2 was used. Within a few minutes the color of the reaction mixture had become brown. The mixture was allowed to stir for an additional 6 days. The resulting dark suspension was filtered and the solvent of the filtrate was removed under reduced pressure. The product was taken up in 2:1 hexane/toluene and filtered, then the solvent of the filtrate was removed under reduced pressure. The residue was slurried in hexane, collected on a frit and dried under reduced pressure to give 0.1743 g, 17.4 percent of zirconium (II) dichloride (1,4-diphenyl-1,3-butadiene)bis(trimethylphosphine).

Example 6

Zirconium (II) dichloride (1,4-diphenyl-1,3-butadiene)bis-(tri-n-propylphosphine)

A) Preparation of zirconium (III) trichloride bis(tri-n-propylphosphine) dimer

In a glove box, lithium powder (0.309 g, 44.47 mmol, low sodium) was added to a toluene solution of zirconium tetrachloride.(tri-n-propylphosphine)$_2$ adduct (prepared from a dropwise addition of 8.9 mL (44.47 mmol) tri-n-propylphosphine to a suspension of 5.18 g (22.24 mmol) $ZrCl_4$ in 100 mL of toluene) and the mixture was then stirred for 12 h at room temperature. The resulting dark green suspension was filtered through a glass frit using diatomaceous earth filter aid. The volatile components were removed under reduced pressure to afford 10.53 g of the product as a green solid. Yield was 91.4 percent.

$^1$H NMR ($C_6D_6$): δ 2.06 (s, br, 12H, $CH_2$), 1.69 (s, br, 12H, $CH_2$), 0.97 (t, $^3J_{H-H}$=7.2 Hz, 18H, $CH_3$). $^{31}$P NMR ($C_6D_6$): δ −9.66 (s).

B) Disproportionation of zirconium (III) trichloride bis(tri-n-propylphosphine) dimer with trans,trans-1,4-diphenyl-1,3-butadiene.

In a glove box, trans,trans-1,4-diphenyl-1,3-butadiene (0.597 g, 2.90 mmol) was added to an equimolar quantity of zirconium (III) trichloride bis(tri-n-propylphosphine) dimer in toluene (50 ml) in a flask and the mixture was then stirred for 1 h at room temperature. The color of the solution turned to purple immediately after 1,4-diphenyl-1,3-butadiene was added. The solvent was removed under reduced pressure and hexane (60 mL) was added to the residue. The resulting suspension was filtered after stirring for ½ h and the solvent of the filtrate was removed in vacuo to afford a dark purple solid. $^1$H and $^{31}$P NMR spectra indicated the material was zirconium (II) dichloride(1,4-diphenyl-1,3-butadiene)bis (tri-n-propylphosphine) along with an equimolar quantity of zirconium tetrachloride bis(tri-n-propylphosphine).

Example 7

Preparation of of zirconium (II) dichloride(1,4-diphenyl-1,3-butadiene)-bis(tri-n-propylphosphine)

In a glove box, lithium powder (0.174 g, 25.03 mmol, low sodium) and 1,4-diphenyl-1,3-butadiene (1.03 g, 5.01 mmol) were added to a toluene solution of zirconium tetrachloride bis(tri-n-propylphosphine) (prepared from a dropwise addition of 2.0 mL (10.01 mmol) tri-n-propylphosphine to a suspension of 1.40 g (6.01 mmol) $ZrCl_4$ in 70 mL of toluene) and the mixture was then stirred overnight at room temperature. The color of the suspension slowly turned to light purple after stirring for 15 min and eventually to dark purple after stirring for a few hours. The resulting dark purple suspension was filtered through a glass frit using diatomaceous earth filter aid and the volatile components were removed under reduced pressure to afford 3.15 g of the desired product as a purple solid. Yield was 91 percent.

$^1$H NMR (C$_6$D$_6$): δ 7.34 (d, $^3$J$_{H-H}$=7.2 Hz, 4H, Ph), 7.23 (t, $^3$J$_{H-H}$=7.2 Hz, 4H, Ph), 6.95 (t, $^3$J$_{H-H}$32 7.2 Hz, 2H, Ph), 6.09 (d, $^3$J$_{H-H}$=8.4 Hz, 2H), 2.57 (d, $^3$J$_{H-H}$=8.4 Hz, 2H), 1.49 (s, br, 12H, CH$_2$), 1.34 (s, br, 12H, CH$_2$), 0.81 (t, $^3$J$_{H-H}$=7.2 Hz, 18H, CH$_3$). $^{31}$P NMR (C$_6$D$_6$): δ −2.58 (s, br). $^{13}$C NMR (C$_6$D$_6$): δ 144.14, 127.57, 125.48, 123.25, 107.35, 88.57, 25.50, 17.85, 16.39.

Example 8

Preparation of of zirconium (II) dichloride(1,4-diphenyl-1,3-butadiene)-bis(triethylphosphine)

In a glove box, lithium powder (0.236 g, 34.0 mmol, low sodium) and trans,trans-1,4-diphenyl-1,3-butadiene (1.40 g, 6.79 mmol) were added to a toluene suspension of zirconium tetrachloride bis(triethylphosphine) (prepared from a dropwise addition of 2.0 mL (13.6 mmol) triethylphosphine to a suspension of 1.90 g (8.15 mmol) ZrCl$_4$ in 70 mL of toluene) and the mixture was then stirred for 16–20 h at room temperature. The color of the suspension turned to light purple after stirring for 5 min and eventually to dark purple after stirring for a few hours. The resulting dark purple suspension was filtered through a glass frit using diatomaceous earth filter aid and the volatile components were removed under reduced pressure to afford 3.83 g of the desired product as a dark purple solid after drying under vacuum for 2 h. Yield was 93 percent.

$^1$H NMR (C$_6$D$_6$): δ 7.34 (d, $^3$J$_{H-H}$=7.2 Hz, 4H, Ph), 7.26 (t, $^3$J$_{H-H}$=7.2 Hz, 4H, Ph), 6.97 (t, $^3$J$_{H-H}$=7.2 Hz, 2H, Ph), 6.05 (d, $^3$J$_{H-H}$=8.4 Hz, 2H), 2.65 (d, $^3$J$_{H-H}$=8.4 Hz, 2H), 1.47 (s, br, 12H, CH$_2$), 0.83 (s, br, 18H, CH$_3$). $^{31}$P NMR (C$_6$D$_6$): δ 3.21 (s, br). $^{13}$C NMR (C$_6$D$_6$): δ 144.22, 128.49, 125.57, 123.44, 107.45, 88.75, 15.64, 8.07.

Example 9

Preparation of rac-dimethylsilanebis(2-methyl-4-phenylinden-1-yl)zirconium (II) (1,4-diphenyl-1,3-butadiene)

Bis(2-methyl-4-phenylindenyllithium)dimethylsilane (1.033 g, 2.15 mmol) and zirconium (II) dichloride (1,4-diphenyl-1,3-butadiene)bis(triethylphosphine) (1.30 g, 2.15 mmol) were mixed in a flask. Dry toluene, 60 mL, was added and the mixture was stirred at room temperature. The color of the suspension slowly turned to red. After 4 h, a $^1$H NMR spectrum of an aliquot taken from the reaction mixture indicated the reaction was complete. The resulting mixture was filtered and the solids were washed with cold hexane to afford a dark red solution. Removal of volatile components gave 1.35 g of the desired product as a red brown solid. Yield was 82.3 percent.

$^1$H NMR (C$_6$D$_6$, 23° C.): δ (ppm) 7.79 (d, $^3$J$_{H-H}$=8.4 Hz, 2H), 7.28–6.98 (m, 18H), 6.87 (d, $^3$J$_{H-H}$=6.9 Hz, 2H), 6.75 (d, $^3$J$_{H-H}$=7.2 Hz, 4H), 5.58 (s, 2H, β-H, Ind), 3.45–3.40 (dd, 2H, β-H, diene), 1.68 (s, 6H, α-Me, Ind), 1.63 (dd, 2H, α-H, diene, partially overlapping with α-Me of Ind peak), 1.22 (s, br, hexane residue), 0.89 (s, 6H, Me$_2$Si), 0.88 (s, br, hexane residue). $^{13}$C NMR (C$_6$D$_6$, 23° C.): δ (ppm) 143.82, 140.28, 136.35, 128.80, 128.74, 124.78, 124.62, 123.82, 122.77, 120.84, 107.93, 89.58, 85.39, 81.30, 31.92 (hexane residue), 23.00 (hexane residue), 16.70, 14.31, 2.19.

Example 10

Preparation of rac dimethylsilanebis(2-methyl-4-phenylinden-1-yl)zirconium (III) 1,4-diphenyl-1,3-butadiene ZrCl$_4$ (0.806 g, 3.46 mmol, 1.2 equiv.) was weighed into a 120 mL glass jar equipped with stirring bar and dissolved in 40 mL toluene. While stirring, triethylphosphine (0.851 mL, 5.76 mmol, 2 equiv.) was added and the mixture was allowed to stir for 5 minutes. To this suspension were added sequentially lithium powder (low sodium, 0.100 g, 14.4 mmol, 5.00 equiv.) and 1,4-diphenyl-1,3-butadiene (0.594 g, 2.88 mmol, 1 equiv.). The mixture was stirred overnight at room temperature. $^1$H and $^{31}$P NMR analysis of an aliquot (1 mL) of the reaction mixture indicated the complete conversion of 1,4-diphenyl-1,3-butadiene. The reaction mixture was filtered through a glass frit using diatomaceous earth filter aid, and the solids were rinsed with 20 mL of toluene.

Bis(2-methyl-4-phenylindenyllithium)dimethylsilane (1.246 g, 2.31 mmol, 0.90 equiv.) was added to the solution and the resulting solution was stirred for 2 hours at room temperature. The reaction mixture was again filtered using diatomaceous earth filter aid, and the solids were rinsed with 20 mL of hexanes. Removal of volatile materials gave 1.893 g of the desired product, the rac-isomer of dimethylsilanebis (2-methyl-4-phenylinden-1-yl)zirconium 1,4-diphenyl-1,3-butadiene. Yield was 98 percent.

Example 11

Preparation of rac dimethylsilanebis(2-methyl-4-phenylinden-1-yl)hafnium (II) 1,4-diphenyl-1,3-butadiene A) Synthesis of hafnium (II) dichloride(1,4-diphenyl-1,3-butadiene)bis(triethylphosphine)

In an inert atmosphere glove box 0.500 g (1.56 mmol) of HfCl$_4$ were washed into a 100 mL flask using 40 mL toluene. To this slurry were added 2 equivalents of PEt$_3$ (0.461 ml, 3.12 mmol). An excess of lithium metal was added (0.108 g, 15.6 mmol) using 5 mL of toluene to aid in the transfer. Finally, 0.322 g (1.56 mmol) of 1,4-diphenyl-1,3-butadiene was added using 10 mL of toluene to aid in the transfer. The flask was sealed and removed from the glove box and placed in a sonicator overnight with stirring. The reaction flask was returned to the glove box. A small aliquot of the reaction mixture was removed, dried in vacuo and extracted with C$_6$D$_6$ for NMR analysis.

$^1$H NMR data, (RT, C$_6$D$_6$, ppm): δ 0.85 and 1.50 (PEt$_3$, broad singlets, 18H and 12H respectively); 2.52 and 6.17 (PhC$_4$H$_4$Ph, doublets, 2H each); 6.9–7.4 (aromatic multiplets).

B) Synthesis of dimethylsilanebis(2-methyl-4-phenylinden-1-yl)hafnium (II) 1,4-diphenyl-1,3-butadiene To the above solution of Hf(II)Cl$_2$ (PEt$_3$)$_2$(1,4-diphenyl-1,3-butadiene) was added 0.750 g (1.56 mmol) of Li$_2$[Me$_2$Si (2-Me-4-Ph-indenyl)$_2$], using 10 mL of toluene to aid in the transfer. The reaction mixture was stirred for 2 hours followed by removal of the toluene in vacuo. The reaction product was extracted with hexane until the filtrate was colorless (approximately 200–250 mL). After removal of the hexane in vacuo, the red solid was recrystallized from toluene at −30° F. The desired product was isolated as red crystals by decanting the mother liquor and drying, giving the product as a toluene solvate.

$^1$H NMR data, (RT, C$_6$D$_6$, ppm): δ 0.849(SiMe$_2$, singlet, 6H); 1.546(PhC$_4$C$_4$Ph, multiplet, 2H); 1.736(2-Me, singlet, 6H); 3.441(PhC$_4$C$_4$Ph, multiplet, 2H); 5.783(Indenyl proton, singlet, 2H); 6.75–7.81 (aromatic multiplets). $^{13}$C NMR data, (RT, C$_6$D$_6$, ppm): δ 2.03 (SiMe$_2$), 16.90 (2-Me), 79.58 (SiC$_{idenyl}$), 82.61 and 85.96 (PhC$_4$H$_4$Ph), 106.53 (C$_{indenyl}$H), 119.47, 120.59, 123.21, 124.22, 124.32, 124.66, 125.64, 127.46, 128.75, 128.84, 129.29, 136.49, 137.84, 140.21, 144.15 (aromatic, indenyl, and toluene aromatic resonances).

Example 12

Preparation of rac dimethylsilanebis(2-methylinden-1-yl)zirconium (II) 1,4-diphenyl-1,3-butadiene)

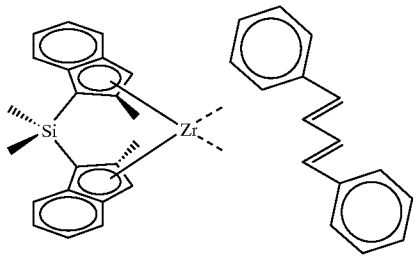

A) Preparation of Dimethylsilyl-bis(2-methylindene), dilithium salt.

Dimethylsilyl-bis(2-methylindene) (1.03 g, 3.25 mmol) was stirred in hexane (50 mL) while n-BuLi (6.51 mmol, 4.07 mL of 1.6 M solution in hexane) was added dropwise. This mixture was allowed to stir overnight during which time a precipitate formed. After the reaction period the mixture was filtered and the desired product was isolated as a pale yellow powder following washing with hexane and drying under vacuum (0.880 g, 82.3 percent yield).

$^1$H (THF-$d_6$): δ 0.72 (s, 6H), 2.46 (s, 6H), 5.86 (s, 2H), 6.36–6.40 (m, 4H), 7.15–7.19 (m, 2H), 7.60–7.70 (m, 2H). $^{13}$C (THF-$d_8$): δ 5.34, 18.60, 97.94, 98.40, 113.82, 114.04, 118.24, 120.11, 132.72, 136.38, 136.89.

B) Preparation of rac-Dimethylsilyl-bis(2-methylindene) Zirconium(trans,trans-1,4-diphenyl-1,3-butadiene)

Dimethylsilyl-bis(2-methylindene), dilithium salt (0.400 g, 1.22 mmol) was added slowly as a solid to a solution of dichlorozirconium(trans,trans-1,4-diphenyl-1,3-butadiene)(PEt$_3$)$_2$ (0.737 g, 1.22 mmol) in toluene (50 mL). The mixture was then filtered and the toluene solution was slowly evaporated. Deep red crystals of the desired product which formed were washed with hexane and dried under vacuum resulting in 0.318 g, 42.8 percent yield of recovered product.

$^1$H (toluene-$d_8$): δ 0.76 (s, 6H), 1.41 (s, 6H), 1.6–1.7 (m, 2H), 3.6–3.7 (m, 2H), 5.16 (s, 2H), 6.56 (d, $^3J_{HH}$=8.4 Hz, 2H), 6.78 (t, $^3J_{HH}$=6.9 Hz, 2H), 6.9–7.0 (m, 8H), 7.0–7.1 (m, 4H), 7.68 (d, $^3J_{HH}$=8.7 Hz, 2H). $^{13}$C (toluene-$d_8$): δ 2.12, 16.13, 80.34, 85.44, 90.69, 108.74, 121.18, 122.27, 122.44, 122.94, 123.28, 124.46, 126.04, 127.77, 129.34, 143.88.

Anal. Calcd. For C$_{38}$H$_{38}$SiZr: C, 74.33; H, 6.24. Found: C, 73.96; H, 5.96.

Example 13

Preparation of rac-Dimethylsilyl-(2-methylindene)(2-methyl-4-phenylindene)Zirconium(trans,trans-1,4-diphenyl-1,3-butadiene)

A) Preparation of Chlorodimethylsilyl-2-methylindene

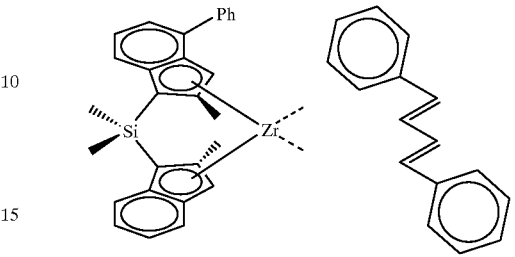

2-Methylindene (5.00 g, 38.4 mmol) was stirred in hexane (30 mL) while n-BuLi (38.4 mmol, 24.0 mL of 1.60 M solution in hexane) was added dropwise. This mixture was allowed to stir for one hour followed by the removal of the volatiles under vacuum. The residue was then dissolved in THF (25 mL) and added dropwise to a solution of Me$_2$SiCl$_2$ (19.8 g, 156 mmol) in THF (75 mL) at 0° C. This mixture was allowed to stir at room temperature overnight. After the reaction period, the volatiles were removed and the residue was extracted and filtered using hexane. Removal of the hexane and vacuum distillation resulted in the isolation of the desired product as a pale yellow oil (5.00 g, 58.4 percent yield).

$^1$H (C$_6$D$_6$): δ 0.063 (s, 3H), 0.16 (s, 3H), 2.07 (s, 3H), 3.25 (s, 1H), 6.41 (s, 1H), 7.06 (t, $^3J_{HH}$=7.4 Hz, 1H), 7.18 (t, $^3J_{HH}$=7.4 Hz, 1H), 7.26 (d, $^3J_{HH}$=7.4Hz, 1H), 7.38 (d, $^3J_{HH}$=7.4 Hz, 1H). $^{13}$C (C$_6$D$_6$): δ −0.66, 1.06, 17.67, 50.20, 120.41, 123.48, 123.77, 126.19, 127.67, 142.79, 145.72.

B) Preparation of Dimethylsilyl-(2-methylindene)(2-methyl-4-phenylindene)

Lithium-2-methyl-4-phenylindenide 0.673 g, 3.17 mmol) in THF (25 mL) was added dropwise to a solution of chlorodimethylsilyl-2-methylindene (0.706 g, 3.17 mmol) in THF (50 mL) at 0° C. This mixture was allowed to stir overnight at room temperature. After the reaction period the volatiles were removed and the residue was extracted and filtered using hexane. Removal of the hexane resulted in the isolation of a yellow oil. This oil was chromatographed using silica gel and hexane/CH$_2$Cl$_2$ (8/2 vol) as the eluent. Collection and isolation of the major middle fraction resulted in the isolation of the desired product as a pale yellow oil upon removal of the volatiles (0.669 g, 49.3 percent yield).

C) Preparation of Dimethylsilyl-(2-methylindene)(2-methyl-4-phenylindene), dilithium salt.

Dimethylsilyl-(2-methylindene)(2-methyl-4-phenylindene) (0.669 g, 1.70 mmol) was stirred in hexane (50 mL) while n-BuLi (3.41 mmol, 2.13 mL of 1.6 M solution in hexane) was added dropwise. This mixture was then allowed to stir overnight during which time a precipitate formed. After the reaction period the mixture was filtered and the salt was washed with hexane and dried under vacuum resulting in the isolation of the desired product as a yellow solid (0.648 g, 94.1 percent yield).

$^1$H (THF-$d_8$): δ 0.73 (s, 6H), 2.48 (s, 3H), 2.50 (s, 3H), 5.86 (s, 1H), 6.15 (s, 1H), 6.3–7.8 (m, 12H). $^{13}$C (THF-$d_8$): δ 5.45, 18.67, 18.89, 98.09, 98.37, 113.80, 114.04, 114.11, 114.28, 118.21, 119.41, 120.10, 125.00, 128.10, 129.07, 129.53, 130.32, 132.67, 136.28, 136.75, 137.35, 138.00, 146.9.

D) Preparation of rac-Dimethylsilyl-(2-methylindene)(2-methyl-4-phenylindene)-Zirconium(trans,trans-1,4-diphenyl-1,3-butadiene)

Dimethylsilyl-(2-methylindene)(2-methyl-4-phenylindene), dilithium salt (0.663 g, 1.64 mmol) was added slowly as a solid to a solution of dichlorozirconium (trans,trans-1,4-diphenyl-1,3-butadiene)(PEt$_3$)$_2$ (0.992 g, 1.64 mmol) in toluene (50 mL). The mixture was then filtered and the toluene was slowly removed. This resulted in the isolation of the desired product as deep red crystals obtained from multiple crops which were then washed with hexane and dried under vacuum giving 0.667 g, 59.1 percent yield.

$^1$H (C$_6$D$_6$): δ 0.80 (s, 3H), 0.84 (s, 3H), 1.49 (s, 3H), 1.64 (s, 3H), 168 (d, $^3J_{HH}$=15 Hz, 1H), 1.74 (d, $^3J_{HH}$=15.3 Hz, 1H), 3.52 (apparent t, $^3J_{HH}$=13.8Hz, 1H), 3.70 (apparent t, $^3J_{HH}$=13.5 Hz, 1H), 5.26 (s, 1H), 5.53 (s, 1H), 6.55 (d, $^3J_{HH}$=8.4 Hz, 1H), 6.60(d, $^3J_{HH}$=7.2 Hz, 1H), 6.77 (t, $^3J_{HH}$6.3 Hz, 1H), 6.8–7.4 (m, 17H), 7.7–7.8 (m, 2H).

Anal. Calcd. For C$_{44}$H$_{40}$SiZr: C, 76.80; H, 5.86. Found: C, 75.91; H, 5.58.

Example 14

Preparation of rac-Dimethylsilane-bis-(5,6,7,8-Tetrahydro-5,5,8,8-tetramethyl-2-methyl-1H-Benz(f)indene)zirconium(trans,trans-1,4-diphenyl-1,3-butadiene)

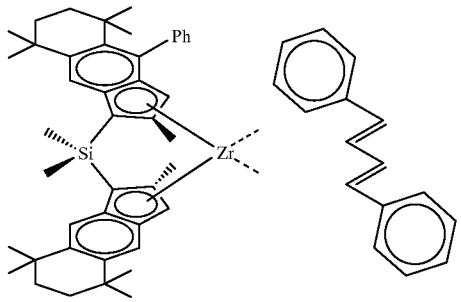

A) Preparation of 1,1',4,4'-Tetramethyl-2,3-dihydronaphthalene.

Benzene (500 mL) and 2,5-dimethyl-2,5-hexanediol (50.00 g, 341.9 mmol) were cooled in an ice-bath as AlCl$_3$ (100.30 g, 752.24 mmol) was added slowly as a solid over 30 minutes under a nitrogen flow such that the mixture never exceeded room temperature. The mixture was held at room temperature for 30 minutes and then heated to 50° C. for 1 hour. The mixture was decanted over crushed ice leaving behind an oily phase. The decanted phase mixture was transferred to an extraction funnel and washed with 1 M HCl (1×200 mL), saturated NaHCO$_3$ (2×200 mL), and H$_2$O (1×200 mL). The organic fraction was then dried over MgSO$_4$. The mixture was filtered and the volatiles were removed, resulting in the isolation of the desired product as a clear colorless oil (53.1 g, 82.5 percent yield).

$^1$H NMR (CDCl$_3$): δ 1.31 (s, 12H), 1.71 (s, 4H), 7.1–7.4 (m, 4H). $^{13}$C NMR (CDCl$_3$): δ 31.67, 34.19, 35.09, 125.50, 126.45, 144.76.

GC-MS Calculated for C$_{14}$H$_{20}$ 188.16, found 188.10.

B) Preparation of 2,3,5,7-Tetrahydro-5,5,8,8-tetramethyl-1H-Benz(f)inden-1-one.

1,1',4,4'-Tetramethyl-2,3-dihydronaphthalene (30.00 g, 159.3 mmol) and 2-bromoisobutyryl bromide (36.62 g, 159.3 mmol) were stirred in CH$_2$Cl$_2$ (500 mL) at 0° C. as AlCl$_3$ (48.86 g, 366.4 mmol) was added slowly as a solid under a nitrogen flow over 30 minutes. This mixture was then allowed to stir at room temperature overnight. After the reaction period the mixture was poured onto crushed ice. The organic layer was then separated and washed with 1 M HCl (1×200 mL), saturated NaHCO$_3$ (1×200 mL) and H$_2$O (1×200 mL). The organic fraction was then dried over MgSO$_4$, filtered, and the volatiles were removed, resulting in the isolation of a dark crystalline residue. Recrystallization from diethylether (0° C.) resulted in the isolation of the desired product as a white crystalline solid (30.7 g, 75.2 percent yield).

$^1$H NMR (CDCl$_3$): δ 1.2–1.4 (m, 15H), 1.71 (s, 4H), 2.6–2.7 (m, 2H), 3.34 (dd, $^1J_{HH}$=17.6 Hz, $^3J_{HH}$=8.7 Hz, 1H), 7.41 (s, 1H), 7.76 (s, 1H). $^{13}$C NMR (CDCl$_3$): δ 16.50, 31.98, 32.09, 32.14, 34.58, 34.84, 35.25, 42.30, 121.92, 124.18, 133.85, 144.77, 149.94, 152.94, 209.05.

GC-MS Calculated for C$_{18}$H$_{24}$O 256.18, found 256.15.

C) Preparation of 5,6,7,8-Tetrahydro-5,5,8,8-tetramethyl-2-methyl-1H-Benz(f)indene 2,3,5,7-Tetrahydro-5,5,8,8-tetramethyl-1H-Benz(f)inden-1-one (14.89 g, 58.08 mmol) and NaBH$_4$ (2.21 g, 58.5 mmol) were stirred in diethylether (200 mL) at 0° C. while EtOH (100 mL) was added slowly. This mixture was allowed to warm slowly to room temperature and then stirred at room temperature overnight. After the reaction period the mixture was poured onto crushed ice and made acidic with HCl. The organic layer was then separated and washed with 1 M HCl (1×100 mL). The volatiles were then removed from the organic layer and the residue refluxed in benzene (300 mL) with p-toluenesulfonic acid (0.12 g) using a Dean-Stark apparatus until no more H$_2$O was evolved. The mixture was then washed with 1 M NaHCO$_3$ (2×100 mL) and the volatiles were removed from the organic layer resulting in the isolation of a yellow oil. Recrystallization from MeOH (0° C.) resulted in the isolation of the desired product as off-white crystals (10.37 g, 74.3 percent yield).

$^1$H NMR (CDCl$_3$): δ 1.43 (s, 12H), 1.82 (s, 4H), 2.24 (s, 3H), 3.36 (s, 2H), 6.54 (s, 1H), 7.33 (s, 1H). 7.45 (s, 1H). $^{13}$C NMR (CDCl$_3$): δ 16.94, 32.25, 34.44, 35.46, 42.44, 117.33, 121.21, 126.80, 139.89, 140.52, 142.55, 143.46, 145.20.

GC-MS Calculated for C$_{18}$H$_{24}$ 240.19, found 240.15.

D) Preparation of 5,6,7,8-Tetrahydro-5,5,8,8-tetramethyl-2-methyl-1H-Benz(f)indene, lithium salt 5,6,7,8-Tetrahydro-5,5,8,8-tetramethyl-2-methyl-1H-Benz(f)indene (3.103 g, 12.91 mmol) was stirred in hexane (75 mL) while n-BuLi (12.9 mmol, 5.16 mL of 2.5 M solution in hexane) was added dropwise. This mixture was then allowed to stir overnight during which time a precipitate formed. The precipitate was collected via filtration, washed with hexane, and dried under vacuum. This product was used without further purification or analysis (2.09 g, 65.6 percent yield).

E) Preparation of Dimethylsilane-bis-(5,6,7,8-Tetrahydro-5,5,8,8-tetramethyl-2-methyl-1H-Benz(f)indene)

5,6,7,8-Tetrahydro-5,5,8,8-tetramethyl-2-methyl-1H-Benz(f)indene, lithium salt (2.087 g, 8.470 mmol) in THF (25 mL) was added dropwise to a solution of Me$_2$SiCl$_2$ (0.547 g, 4.24 mmol) in THF (50 mL) at 0° C. This mixture was then allowed to stir at room temperature overnight. After the reaction period the volatiles were removed and the residue was extracted and filtered using hexane. Removal of the hexane under vacuum resulted in the isolation of the desired product as a white glassy foam (2.27 g, 99.9 percent yield).

$^1$H NMR (C$_6$D$_6$): δ −0.26 (s, 3H), −0.11 (s, 3H), 1.29 (s, 6H), 1.31 (s, 6H), 1.34 (s, 6H), 1.66 (s, 8H), 2.05 (s, 6H), 3.58 (s, 2H), 6.55 (s, 2H), 7.42 (s, 2H), 7.56 (s, 2H). $^{13}$C NMR (C$_6$D$_6$): δ 5.20, 4.69, 17.88, 32.48, 32.70, 34.53, 35.78, 46.68, 117.96, 121.67, 127.10, 139.56, 142.01, 142.97, 143.68, 146.51.

F) Preparation of Dimethylsilane-bis-(5,6,7,8-Tetrahydro-5,5,8,8-tetramethyl-2-methyl-1H-Benz(f)indene), dilithium salt Dimethylsilane-bis-(5,6,7,8-Tetrahydro-5,5,8,8-tetramethyl-2-methyl-1H-Benz(f)indene) (1.271 g, 2.370 mmol) was stirred in hexane (75 mL) while n-BuLi (5.210 mmol, 2.08 mL of 2.5 M solution in hexane) was added dropwise. This mixture was allowed to stir overnight during which time a sticky residue precipitated out of solution. After the reaction period the volatiles were removed and the residue was washed twice with cold hexane. The residue was then pumped dry under vacuum resulting in the isolation of the desired product as a yellow solid which was used without further purification or analysis (1.05 g, 80.7 percent yield).

$^1$H (THF-d$_8$): δ 0.72 (s, 6H), 1.18 (s, 12H), 1.21 (s, 12H), 1.59 (s, 8H), 2.37 (s, 6H), 5.70 (s, 2H), 7.12 (s, 2H), 7.49(s, 2H). $^{13}$C (THF-d$_8$): δ 5.70, 18.60, 33.61, 33.82, 34.74, 35.01, 37.49, 37.55, 96.08, 96.82, 115.20, 117.96, 130.86, 130.96, 131.50, 135.89, 137.04.

G) Preparation of rac-Dimethylsilane-bis-(5,6,7,8-Tetrahydro-5,5,8,8-tetramethyl-2-methyl-1H-Benz(f)indene)zirconium(trans,trans-1,4-diphenyl-1,3-butadiene)

Dimethylsilane-bis-(5,6,7,8-Tetrahydro-5,5,8,8-tetramethyl-2-methyl-1H-Benz(f)indene), dilithium salt (0.400 g, 0.730 mmol) was added slowly as a solid to a solution of dichlorozirconium(trans,trans-1,4-diphenyl-1,3-butadiene)(PEt$_3$)$_2$ (0.441 g, 0.730 mmol) in toluene (50 mL). The mixture was then filtered and the toluene slowly evaporated. This resulted in the isolation of the desired product as deep red crystals obtained from multiple crops which were then washed with hexane and dried under vacuum (0.300 g, 49.4 percent yield).

$^1$H (toluene-d$_8$): δ 1.03 (s, 6H), 1.2 (m, 12H), 1.52 (s, 6H), 1.9–2.1 (m, 2H), 2.0–2.1 (m, 4H), 3.9–4.1 (m, 2H), 5.17 (s, 2H), 6.8–6.9 (m, 6H), 6.97 (s, 2H), 7.0–7.1 (m, 4H), 7.95 (s, 2H). $^{13}$C (toluene-d$_8$): δ 2.38, 16.35, 32.04, 32.77, 33.90, 34.06, 34.91, 35.16, 35.23, 35.44, 79.11, 84.56, 90.39, 106.91, 119.95, 121.84, 122.02, 123.78, 124.17, 125.94, 141.37, 143.80, 144.29.

Anal. Calcd. For C$_{54}$H$_{64}$SiZr: C, 77.92; H, 7.75. Found: C, 78.29; H, 7.67.

Polymerizations

A) Ethylene/1-octene Copolymerization

Polymerizations are conducted in a two-liter Parr reactor that is charged with about 740 mL of mixed alkanes solvent and approximately 118 g of 1-octene. Hydrogen, (Δ170 kPa) is added by differential pressure expansion from a 75 mL addition tank. The reactor is charged with ethylene (3.4 MPa) heated to 140° C. and allowed to equilibrate. The desired amount of transition metal component (1 μmole) and cocatalyst (a 1/6 molar ratio of tris(pentafluorophenyl)borane and di(isobutyl)(2,6-di(t-butyl)-4-methylphenoxy) aluminum)) as solutions in toluene, were premixed in the drybox to give a 1:1:6 Ti:B:Al molar ratio and charged to the polymerization reactor through a stainless steel transfer line using nitrogen and about 10 mL of a toluene "chaser". The polymerization conditions are maintained for 15 minutes with ethylene on demand. Heat is continuously removed from the reaction through an internal cooling coil. The resulting solution is removed from the reactor, quenched with isopropyl alcohol, and stabilized by addition of a hindered phenol antioxidant (Irganox™ 1010 from Ciba Geigy Corporation). The solvent is removed in a vacuum oven set at 140° C. by heating the polymer solution for about 16 hours. Results are shown in Table 1.

TABLE 1

| Run | catalyst | Efficiency (g polymer/μg Zr) | Density (g/cc) | Melt Index (g/10 min) | Mw/Mn |
|---|---|---|---|---|---|
| 1 | Ex. 10 | 0.75 | 0.893 | 5.4 | 75,200/32,600 = 2.30 |
| 2 | Ex. 12 | 0.67 | 0.921 | 11.0 | 64,100/32,100 = 1.99 |
| 3 | Ex. 13 | 0.31 | 0.912 | 13.0 | 60,300/28,300 = 2.13 |
| 4 | Ex. 14 | 0.88 | 0.920 | 51.4 | 42,500/17,200 = 2.46 |

B) Propylene Polymerization

Propylene polymerizations were performed in a two-liter, jacketed, Autoclave Engineer's Zipper-Clave™ that was charged with 625 g mixed alkanes solvent and about 150 g propylene. Hydrogen, (Δ350 kPa) was added by differential pressure expansion from a 75 mL addition tank. The reactor was heated to 70° C. and allowed to equilibrate. The desired amount of transition metal component (1 μmole) and cocatalyst (either (a 1/6 molar ratio of tris(pentafluorophenyl) borane and di(isobutyl)(2,6-di(t-butyl)-4-methylphenoxy) aluminum) (A) or methyldi(octadecyl)ammonium(di(ethyl) aluminumoxyphenyl)tris(pentafluorophenyl)borate) (B) as solution in toluene, were premixed in the drybox to give a 1:1 Ti:B molar ratio and charged to the polymerization reactor through a stainless steel transfer line using nitrogen and about 10 mL of a toluene "chaser". The polymerization conditions were maintained for 15 minutes. Heat was continuously removed from the reaction through a cooling coil in the jacket. The resulting solution was removed from the reactor, quenched with isopropyl alcohol, and stabilized by addition of a hindered phenol antioxidant (Irganox™ 1010 from Ciba Geigy Corporation). The solvent was removed in a vacuum oven set at 140° C. by heating the polymer solution for about 16 hours. Results are shown in Table 2.

TABLE 2

| Run | catalyst | cocatalyst | Efficiency (g polymer/μg Zr) | Tm (° C.) | Mw/Mn |
|---|---|---|---|---|---|
| 5 | Ex.10 | A | 117 | 157.2 | 192,000/107,000 = 1.79 |
| 6 | " | B | 128 | 157.8 | 61,000/32,600 = 1.87 |
| 7 | Ex.12 | A | 115 | — | — |
| 8 | " | B | 212 | 146.8 | 79,000/42,900 = 1.84 |
| 9 | Ex.13 | A | 2 | 154.0 | 38,900/10,300 = 3.78 |
| 10 | " | B | 12 | 155.0 | 124,000/65,100 = 1.90 |
| 11 | Ex.14 | A | 226 | 147.0 | 60,500/34,200 = 1.76 |
| 12 | " | B | 212 | 144.8 | 61,000/32,600 = 1.87 |

C) Propylene Polymerization With Supported Catalysts

Triethylaluminum (30 μmoles, 0.016 mL of 0.19 M solution in toluene) was added to a solution of methyl(dioctadecyl)ammonium(p-hydroxyphenyl)-tris (pentafluorophenyl)borate (30 μmoles, 0.395 mL of 0.076 M solution in toluene) and the mixture was shaken for 5 minutes. This mixture was then added dropwise to solid silica (0.50 g, Grace-Davison 948, available from Grace-Davison Chemical Company). The silica was shaken and broken apart using a spatula until the sample was flowable. This solid was then shaken for an additional 10 minutes. Hexane (4.00 mL) was then added to the solid which was then shaken for another 15 minutes. The metal complex (20 μmoles, 4.00 mL of a 0.005 M solution in toluene) was then added to the mixture and shaken for 2 hours. The slurry was then filtered, washed with hexane (2×20 mL), and dried under vacuum overnight.

Propylene was again polymerized using conditions substantially as reported in section B), excepting the above supported catalyst was used. Results are contained in Table 3.

TABLE 3

| Run | catalyst | Efficiency (g polymer/mg Zr) | Tm °C. | Mw/Mn |
|-----|----------|------------------------------|--------|-------|
| 13  | Ex. 10   | 38                           | 141.1  | 57,600/21,000 = 2.75 |
| 14  | Ex. 12   | 45                           | 145.2  | 96,100/29,600 = 3.24 |
| 15  | Ex. 13   | 164                          | 149.4  | 131,000/40,800 = 3.21 |
| 16  | Ex. 14   | 779                          | 151.0  | 236,000/65,000 = 3.59 |

What is claimed is:

1. A process for preparing a compound according to the formula: $MX_2D(L')_k$ the steps of the process comprising contacting in any order, in an inert diluent, and optionally in the presence of a Lewis base, a Group 4 metal complex corresponding to the formula, $M^1X_4(L')_k$ with a reducing agent to prepare a dimeric compound corresponding to the formula:

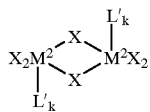

and subsequently or simultaneously contacting said dimeric compound with the diene D, wherein M is titanium, zirconium or hafnium in the +2 formal oxidation state;

$M^1$ is titanium, zirconium or hafnium in the +4 formal oxidation state;

$M^2$ is titanium, zirconium or hafnium in the +3 formal oxidation state;

D is a neutral, substituted derivative of 1,3-butadiene, substituted with one or more hydrocarbyl groups, silyl groups, hydrocarbylsilyl groups, silylhydrocarbyl groups, or mixtures thereof, at least one of said substituents being located at the 1- or 4-position, said D having from 5 up to 40 atoms other than hydrogen;

X independently each occurrence is a monovalent anionic leaving group of up to 50 atoms other than hydrogen, and optionally, two X groups (excluding bridging anion X groups) are joined together thereby forming a divalent anionic leaving group;

L' is a Lewis base, and k is a number from 0 to 3.

2. The process of claim 1, wherein M is zirconium, X is chloride, L' is triethylphosphine or tripropylphosphine, D is 1,4-diphenylbutadiene, and the reducing agent is lithium.

3. A process according to claim 1 wherein L independently each occurrence is a cyclic or polycyclic hydrocarbyl group or a heteroatom containing cyclic or polycyclic hydrocarbyl group, or such group further substituted with one or more substituents independently selected from the group consisting of hydrocarbyl, silyl, tri(hydrocarbyl)silyl; tri(hydrocarbyl)germyl, halo, cyano, halohydrocarbyl, halocarbyl, N,N-di(hydrocarbyl)amino, hydrocarbyloxy, and tri(hydrocarbyl)siloxy, said substituent having up to 20 atoms other than hydrogen, or optionally, two such substituents may be bonded together.

4. A process according to claim 3, wherein L is cyclopentadienyl, indenyl, fluorenyl, cyclohexadienyl, cycloheptadienyl, benzoindenyl, boratabenzenyl, s-indacenyl, gem-dimethylacenaphthalenyl, or cyclopenta(I)phenanthrenyl, or a substituted derivative thereof bearing one or more substituents independently selected from the group consisting of hydrocarbyl, silyl, tri(hydrocarbyl)silyl; tri(hydrocarbyl)germyl, halo, cyano, halohydrocarbyl, halocarbyl, N,N-di(hydrocarbyl)amino, hydrocarbyloxy, and tri(hydrocarbyl)siloxy, said substituent having up to 20 atoms other than hydrogen, or optionally, two such substituents may be bonded together.

* * * * *